United States Patent
Lvovich et al.

(10) Patent No.: US 7,259,575 B2
(45) Date of Patent: *Aug. 21, 2007

(54) METHOD FOR ON-LINE FUEL-DILUTION MONITORING OF ENGINE LUBRICANT

(75) Inventors: Vadim F. Lvovich, Cleveland Heights, OH (US); Frederick P. Boyle, Kirtland, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 175 days.

This patent is subject to a terminal disclaimer.

(21) Appl. No.: 11/101,978

(22) Filed: Apr. 8, 2005

(65) Prior Publication Data

US 2006/0229776 A1    Oct. 12, 2006

(51) Int. Cl.
*G01R 27/08* (2006.01)
*G01R 27/26* (2006.01)

(52) U.S. Cl. ...................... 324/698; 324/667
(58) Field of Classification Search ........ 324/698, 324/664, 663, 667, 681
See application file for complete search history.

(56) References Cited

U.S. PATENT DOCUMENTS

| | | | |
|---|---|---|---|
| 4,646,070 A * | 2/1987 | Yasuhara et al. | 340/603 |
| 5,025,219 A * | 6/1991 | Gaspard | 324/447 |
| 5,331,287 A | 7/1994 | Yamagishi et al. | 324/724 |
| 5,518,590 A | 5/1996 | Fang | 205/780.5 |
| 5,540,086 A | 7/1996 | Park et al. | 73/53.05 |
| 5,656,767 A | 8/1997 | Garvey, III et al. | 73/61.44 |
| 5,817,928 A * | 10/1998 | Garvey et al. | 73/53.05 |

(Continued)

FOREIGN PATENT DOCUMENTS

EP    0531585 A1    3/1993

(Continued)

OTHER PUBLICATIONS

Electrical Conductivity Method for Evaluation of Oxidative Degradation of Oil Lubricants; Lubrication Engineering, vol. 48, 7, 539-544; 1991, by Atsushi Sato and Takashi Oshika.

(Continued)

*Primary Examiner*—Anjan Deb
(74) *Attorney, Agent, or Firm*—Teresan W. Gilbert; Michael F. Esposito

(57) ABSTRACT

A method for determining a fuel-dilution condition of a lubricant used in transportation and industrial equipment. The method uses apparatus that applies a high frequency and optionally a low frequency oscillating signal to electrodes immersed in the fluid and quantifies fluid response to the signals. Apparatus can further include means to control the lubricant temperature, or a temperature sensor to monitor the lubricant temperature at the electrodes. The method monitors response of the lubricant to the applied electrical signals and determines ratios of lubricant properties. The high-frequency lubricant property ratio or change of high frequency lubricant property as a function of a lubricant use-measure is compared to a predicted ratio based on lubricant use and an estimate of the lubricant's fuel dilution determined. The optional low-frequency lubricant property ratio is compared to thresholds to determine when the lubricant loses the ability to control fuel dilution. The method outputs information relevant to the fuel-dilution condition of the lubricant.

23 Claims, 8 Drawing Sheets

U.S. PATENT DOCUMENTS

| | | | |
|---|---|---|---|
| 5,824,889 A | 10/1998 | Park et al. | 73/116 |
| 5,889,200 A | 3/1999 | Centers et al. | 73/53.01 |
| 5,933,016 A | 8/1999 | Kauffman et al. | 324/698 |
| 6,028,433 A | 2/2000 | Cheiky-Zelina et al. | 324/663 |
| 6,217,745 B1 | 4/2001 | Fang | 205/775 |
| 6,268,737 B1 * | 7/2001 | Marszalek | 324/663 |
| 6,278,281 B1 * | 8/2001 | Bauer et al. | 324/441 |
| 6,535,001 B1 | 3/2003 | Wang | 324/698 |
| 6,693,444 B2 * | 2/2004 | Lin et al. | 324/698 |
| 6,861,851 B2 * | 3/2005 | Lvovich et al. | 324/698 |
| 2002/0125899 A1 | 9/2002 | Lvovich et al. | 324/663 |
| 2004/0036587 A1 | 2/2004 | Heremans et al. | 324/698 |
| 2004/0075488 A1 | 4/2004 | Lvovich et al. | 324/707 |
| 2004/0263187 A1 * | 12/2004 | Hayashi et al. | 324/698 |
| 2006/0214671 A1 * | 9/2006 | Wooton et al. | 324/698 |

FOREIGN PATENT DOCUMENTS

| | | |
|---|---|---|
| EP | 1014082 A2 | 6/2000 |
| EP | 1098197 A2 | 5/2001 |
| JP | 406082408 | 3/1994 |
| WO | WO91/09922 | 7/1991 |
| WO | WO 03/054482 A2 | 7/2003 |

OTHER PUBLICATIONS

Development of an On-Board Type Oil Deterioration Sensor; SAE Technical Paper Series, Oct. 1993.

Proceedings of the Symposium on Chemical Sensors; The Electrochemical Society, Inc., Proceedings vol. 87-9; Turner.

In-Situ Oil Condition Monitoring in Passenger Cars; Lubrication Engineering, vol. 50, 8, 605-611; Lee et al.

Development of an Automatic Engine Oil-Change Indicator System; SAE Technical Paper Series; Schwartz et al.; Feb. 23-27, 1987.

A Capacitive Oil Deterioration Sensor; Saloka et al.

Oil Maintenance Tester: A New Device to Detect the Degradation Level of Oils; Lubrication Engineering; Nov. 1986; Kato et al.

In Situ Electrochemical Sensor for Measurement in Nonconductive Liquids; J. Electrochemical Society, vol. 140, No. 3, Mar. 1993; Joseph et al.

The development of in situ electrochemical oil-condition sensors; Sensors and Actuators B, 17 (1994) 179-185; Wang et al.

In situ monitoring of high-temperature degraded engine oil condition with microsensors; Sensors and Actuators B, 20 (1994) 49-54; Lee et al.

The application of a.c. impedance technique for detecting glycol contamination in engine oil; Sensors and Actuators B 40 (1997) 193-197; Want et al.

"Smart Sensing" of Oil Degradation and Oil Level Measurements in Gasoline Engines; SAE Technical Paper Series; Mar. 6-9, 2000; Basu et al.

Development of an On-Board Type Oil Deterioration Sensor; SAE Technical Paper Series; Oct. 18-21, 1993; Morishita et al.

Low Cost Oil Deterioration Sensor for On-Board Diagnostics; Park et al.

* cited by examiner

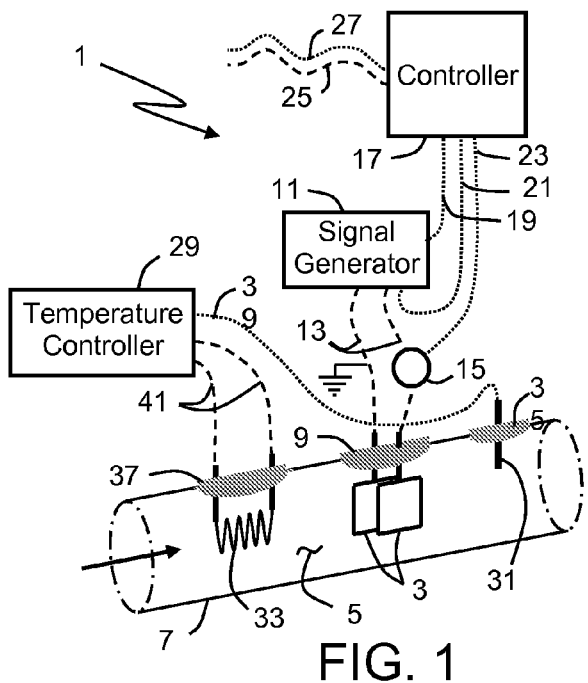
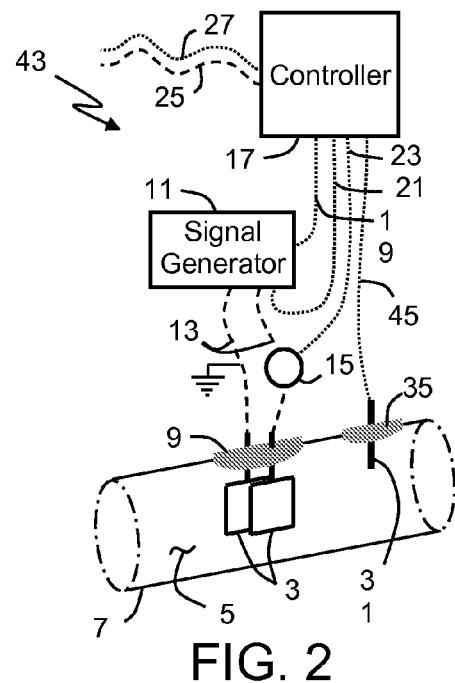
FIG. 1
FIG. 2
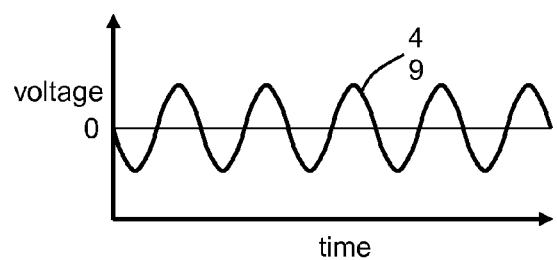
FIG. 3
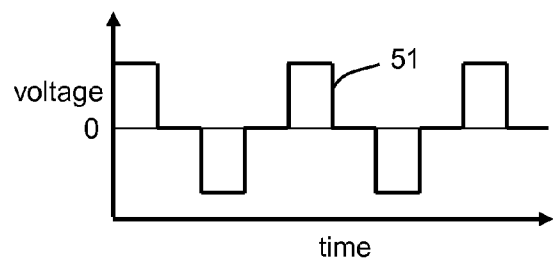
FIG. 4

METHOD FOR ON-LINE FUEL-DILUTION MONITORING OF ENGINE LUBRICANT

BACKGROUND OF THE INVENTION

The present invention is a method for monitoring a condition of a lubricant. The invention has particular benefit for monitoring fuel content, commonly referred to as fuel dilution, of an engine lubricant and in determining when a lubricant can no longer provide desired engine performance and life.

Lubricating oil is critical to the performance and operational life of an internal combustion engine. When the lubricant has appropriate viscosity for the required hydrodynamic film, detergents and dispersants to suspend and/or neutralize undesired contaminants, and surface active chemicals to protect engine component surfaces, the lubricant allows for long, efficient engine operation by reducing friction, wear and corrosion of engine components. In general, a lubricant's performance characteristics change with use and age, and a lubricant reaches the end of its useful life when any one of the lubricant's performance properties is out side a desired range. Using a lubricant past the end of its useful life reduces engine performance and life, possibly catastrophically.

Most often a lubricant reaches end-of-life due to normal consumption, degradation or depletion of base oil and/or additives by an engine in good condition, operating under a typical duty cycle and in a proper environment for an application. A lubricant, however, can also reach end-of-life due to abnormal engine condition, operating cycle and/or operating environment. An example of an abnormal engine condition is a fouled fuel injector that, instead of spraying a fine mist of fuel into a cylinder, either pre- or post-combustion, sprays an abnormal amount of fuel onto the cylinder wall. Fuel sprayed onto the cylinder wall can mix with a thin protective lubricant layer, thereby contaminating the lubricant with fuel. Fuel dilution degrades performance of the lubricant, which reduces the lubricant's useful life.

An engine operator wants to maximize the lubricant value by allowing the lubricant to remain in an engine and to not be replaced with fresh, i.e. unused, lubricant until the lubricant is near or at the end of its useful life. However, with the complexity of lubricant degradation, due to both normal and abnormal variables, accurate determination of the lubricant's condition has traditionally required off-line laboratory tests. Most operators, however, do not consider such test to be cost and/or time effective and instead choose to estimate lubricant condition when making a lubricant change decision. Change intervals are often based on operation parameters that are easily measured by the operator, such as time of operation, distance driven, and/or fuel use. Many engine manufacturers have developed algorithms to help operators make a change decision based on one or more engine operating parameters that may not easily be monitored by the operator. In either case, no actual lubricant condition information is used, and the change interval may not be optimized even for normal lubricant degradation modes, and is generally accepted to not be optimized if abnormal lubricant degradation occurs from, for example fuel dilution.

Recently, sensors for real-time, on-board measurement of a lubricant's electrical, optical or other properties have been introduced; see "Determining Proper Oil and Filter Change Intervals: Can Onboard Automotive Sensors Help?", Sabrin Khaled Gebarin and Jim Fitch, Practicing Oil Analysis, March-April 2004. Many of these sensors provide an output that is a function of a measured lubricant property with no actual analysis of the fluid condition. In general, sensors without condition analysis are of limited value to engine or equipment manufacturers. To overcome this limitation, some sensors attempt to provide a complete solution with hardware and/or software that interpret fluid condition based on a measured property. The method disclosed in Lvovich, et al., U.S. patent application Ser. No. 10/271,885, provides a cost effective, relatively complete fluid condition analysis based on a multitude of a fluid's electrical impedance responses. While this method has been shown effective in determining when a lubricant reaches end-of-life under normal lubricant degradation, the method, except for a water/coolant leak, does not determine if end-of-life occurred due to an abnormal event. Electrical impedance methods, do not determine if end-of-life was primarily due to fuel dilution, or identify that fuel dilution is occurring before reaching end-of-life.

There remains a need for a cost-effective, on-line, lubricant monitoring sensor to provide a real-time determination if fuel dilution is occurring in order that the lubricant and the equipment using the lubricant can be maintained to provide desired performance and life.

The present invention provides a sensor and method for on-line determining lubricant condition based on a property that is consistent with fuel content while the lubricant is in use in industrial or transportation applications.

SUMMARY OF THE INVENTION

The present invention relates to a method to monitor fuel content in lubricants used in transportation and industrial applications.

The invention comprises applying a high frequency signal between electrodes immersed in the monitored lubricant and measuring the lubricant response to the applied signal and determining the lubricant permittivity, or permittivity equivalent, and comparing the determined lubricant permittivity to a permittivity predicted based on a lubricant use-measure to determine the fuel-dilution condition of the lubricant.

Further, the invention in another embodiment comprises applying a high frequency signal between electrodes immersed in the monitored lubricant, measuring the lubricant response to the applied signal and determining the lubricant permittivity or permittivity equivalent, comparing the change of the determined lubricant permittivity as a function of a lubricant use-measure to a predicted permittivity change based on the lubricant use-measure to determine the fuel-dilution condition of the lubricant.

Further, the invention in another embodiment comprises applying a high-frequency signal and a low-frequency signal between electrodes immersed in the monitored lubricant, measuring the lubricant responses to the applied signals and determining a high-frequency lubricant permittivity or permittivity equivalent and a low-frequency lubricant real impedance or real impedance equivalent, comparing the determined high-frequency permittivity to a high-frequency permittivity predicted based on a lubricant use-measure and comparing the ratio of determined low-frequency real impedance to the peak determined low-frequency real impedance, to at least one real impedance threshold to determine the fuel-condition of the lubricant.

Further, the invention in another embodiment comprises applying a high-frequency signal and a low-frequency signal between electrodes immersed in the monitored lubricant, measuring the lubricant responses to the applied signals and determining a high-frequency lubricant permittivity or permittivity equivalent and a low-frequency lubricant real impedance or real impedance equivalent, comparing the change of the determined high frequency lubricant permittivity as a function of a lubricant use-measure to a predicted high frequency permittivity change based on the lubricant use-measure and comparing the ratio of determined low-frequency real impedance or equivalent to the peak determined low-frequency real impedance, to at least one impedance threshold to determine the fuel-condition of the lubricant.

One feature of the invention is that the high-frequency signal is at least one of the following: essentially sinusoidal of an essentially define frequency, or essentially non-sinusoidal, for example a pulsed signal, of frequency defined by the Fourier-Transform base frequency, that is the lowest frequency of a composite of sine waves that can represent the essentially non-sinusoidal signal.

Another feature of the invention is that the frequencies of the applied signals are predetermined as a function of apparatus electrode geometry, fluid temperature or temperature range, chemical composition of the fluid being monitored or combinations thereof.

Another feature of the invention is the lubricant use-measure can be based on at least one of the following: equipment use-measures, a lubricant condition determined by other than the applied signals of this invention, and combinations thereof.

Another feature of the invention is that equipment use-measures may include one or more of the following: operating time, energy output, distance traveled, number of operating cycles, equipment temperature, fuel consumption, start/stop cycles and combinations thereof.

Another feature of the invention is that a lubricant condition may include one or more of the following: lubricant response to one or more signals applied at frequencies other than the frequencies of this invention, viscosity, IR absorption, lubricant temperature and combinations thereof.

Another feature of the invention is that the predicted response or change of response based on the lubricant use-measure can be predicted using at least one of the following: a formula, a look-up table or combinations thereof.

Another feature of the invention is that the predicted response or change of response based on the lubricant use-measure can be updated each time the lubricant is changed by extrapolating response data near zero use of the fresh lubricant.

Another feature of the invention is that a formula or look-up table used to calculate a high-frequency comparison value can be fixed or can be updated to allow for changes in: lubricant formulation, equipment operation or combinations thereof.

Another feature of the invention is that a threshold used for the low-frequency ratio comparison can be fixed, or can be updated to allow for changes in: lubricant formulation, equipment operation or combinations thereof.

Another feature of the invention is that for lubricants that operate over a limited temperature range, preferably less than 5° C., more preferably less than 2° C., and most preferably less than 1° C., lubricant response can be measured without controlling the lubricant temperature or without converting, compensating or correcting the response for the effect of temperature variation.

Another feature of the invention is that the lubricant response can be measured by controlling the lubricant temperature to an essentially fixed temperature or can be converted, compensated or corrected to minimize the effect of temperature variation on lubricant responses using appropriate formulae or look-up tables.

Another feature of the invention is that a formula or look-up table used to convert, compensate or correct lubricant responses for temperature variations can be permanently fixed, or can be updated, by values inputted to the method or automatically determined by measuring response changes as the lubricant changes temperature between two temperature thresholds at greater than a set rate, to allow for changes in formulation of fresh lubricant added to the equipment.

Another feature of the invention is that the lubricant condition output can indicate: the lubricant has reached the end of its useful live, the lubricant is near the end of its useful life, the approximate amount of fuel in the lubricant, the approximate remaining useful life of the lubricant, response and use data for further lubricant condition analysis, or combination thereof.

Another feature of the invention is that the lubricant condition output can be provided to: memory for later download, a signaling device that can be observed or received by for example an operator, a service facility or function, a signal processor that uses or converts the output to for example control engine operation or modify lubricant properties, or combinations thereof.

The present invention may be more readily apparent from the following figures.

BRIEF DESCRIPTION OF THE FIGURES

FIG. 1 is a schematic representation of an apparatus that can be used with the current invention, where the apparatus controls lubricant temperature.

FIG. 2 is a schematic representation of an apparatus, wherein the lubricant temperature is monitored but not controlled.

FIG. 3 is a graphic representation of a sinusoidal signal that can be applied to a lubricant by an apparatus of the current invention.

FIG. 4 is a graphic representation of a non-sinusoidal high frequency signal that can be applied to a lubricant by an apparatus of the current invention.

DETAILED DESCRIPTION OF THE INVENTION

Figure 5:
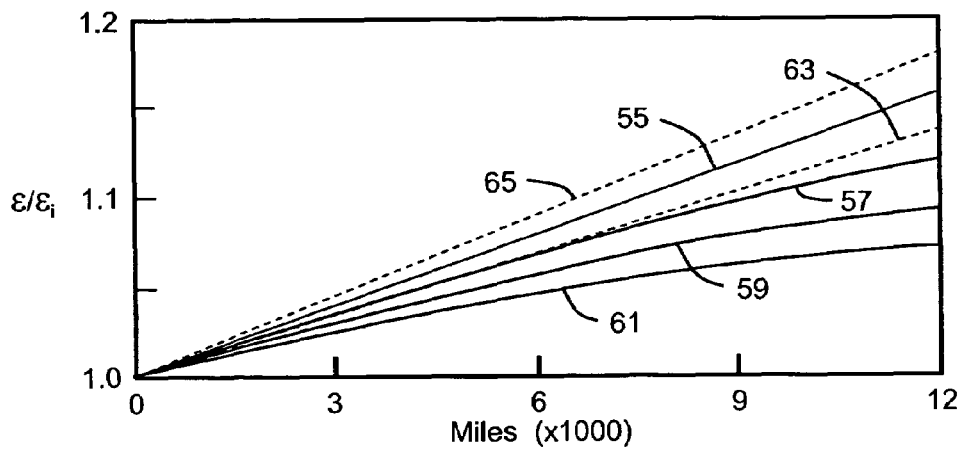
FIG. 5 is a graphic representation of the high-frequency permittivity ratio, that is, the measured permittivity divided by the permittivity of the lubricant when fresh $\epsilon/\epsilon_i$, response of a diesel engine oil with and without fuel dilution as a function of engine use.

The invention relates to a method for on-line monitoring a condition that is consistent with fuel content of a lubricant, in particular an engine lubricant, used in industrial and transportation applications.

FIG. 1 is a schematic illustration of an apparatus 1 that can be used to collect appropriate data required for the on-line monitoring and detecting condition of a lubricant. Apparatus 1 includes essentially parallel electrodes 3 immersed in lubricant 5, in conduit 7. Electrodes 3 are fixedly held and electrically isolated by mount 9. Apparatus 1 also includes signal generator 11 that sequentially supplies a high-frequency voltage signal of fixed amplitude and frequency and a low-frequency voltage signal of fixed amplitude and frequency through electrical conduits 13, to electrodes 3. The high-frequency voltage signal supplied by signal generator 11 can be an essentially sine wave illustrated by curve 49 in FIG. 3 where the voltage signal oscillates essentially sinusoidally about zero volts with the number of complete oscillations per time being the frequency of the signal. The high-frequency voltage signal supplied by signal generator 11 can be non-sinusoidal as illustrated by curve 51 in FIG. 4 where the voltage signal oscillates about zero volts with a frequency defined by the Fourier transform base frequency as known in the art. The low-frequency signal supplied by signal generator 11 is an essentially sine wave illustrated by curve 49 of FIG. 3. The frequencies of signal generator 11 are preset based on the geometry of electrode pair 3 and by type and operating temperature or temperature range and chemical composition of lubricant 5. The required frequencies increase as a function of the increase of the electrode area divided by the separation of electrodes 3. The frequencies also increase as a function of lubricant temperature increase. Frequency variation as a function of lubricant composition is quite complex and is often determined for a particular lubricant-type; however, typical engine lubricant compositions are sufficiently similar that frequency variations are insignificant. In general, frequencies and the geometry and separation of electrodes 3 are chosen to be appropriate for a typical range of temperatures and lubricants 5 that are used in a particular application. In one embodiment for a typical engine lubricant, with operating temperature in the range from about 40° C. to about 120° C., using parallel-plate electrodes with an area to gap ratio of about 300 cm, the preset high frequency of signal generator 11 is on the order of about 1 MHz and the preset low frequency is on the order of about 100 Hz. In another embodiment, for typical electrodes, temperature ranges and engine lubricants, the preset high frequency of signal generator 11 is typically in the range from about 10 kHz to about 10 MHz and the preset low frequency is typically in the range of about 1 Hz to about 1 kHz. Again referring to FIG. 1, one electrical conduit 13 of signal generator 11 is grounded for a voltage reference and the other conduit 13 includes a current sensor 15, which measures electrical current flow through conduit 13. Apparatus 1 also includes controller 17 with electrical conduit 19 for powering signal generator 11, electrical conduit 21 for monitoring output voltage of signal generator 11, and electrical conduit 23 for monitoring current flow measured by current sensor 15. Controller 17 also has electrical conduit 25 to receive power and electrical conduit 27 to communicate information either to or from the controller 17.

Apparatus 1 includes a temperature controller 29, thermocouple 31, and heater 33. Thermocouple 31 and heater 33 are fixedly held in conduit 7 by mounts 35 and 37, respectively and electrically communicate with temperature controller 29 via electrical conduits 39 and 41, respectively, such that in operation controller 29 applies power to heater 33 through conduits 41 to maintain the temperature of the lubricant 5 flowing past the thermocouple 31 at a determined fixed temperature; thereby maintaining the lubricant temperature at electrodes 3.

In operation, lubricant 5 flows through conduit 7, in the direction shown by the arrow, with a portion of the lubricant flowing between electrodes 3, power is applied to controller 17 through electrical conduit 25. Temperature controller 29 monitors the temperature of lubricant 5 with thermocouple 31 and electrical conduit 39 and applies appropriate power through conduits 41 to heater 33 to maintain the lubricant in the conduit at a preset temperature. The method of this invention determines when controller 17 powers signal generator 11 to apply signals through conduits 13 and electrodes 3 to fluid 5. The electrical response of lubricant 5 to the applied signals causes current to flow and to be measured by current sensor 15. Controller 17 monitors the applied signal and the corresponding current flow through electrical conduits 19, 21 respectively, and compares magnitude and phase of the voltage and current signals to calculate electrochemical impedance of the lubricant 5. The method of this invention uses the impedance data to determine condition of lubricant 5. Controller 17 can receive information useful for the lubricant condition determination through electrical conduit 27, for example, information that a volume of fresh lubricant was made or that an essentially complete lubricant exchange has occurred, or updates of values or functions used in the lubricant condition determination can be received. A method of this invention communicates information about the lubricant condition from controller 17 through electrical conduit 27. The lubricant condition information can be immediately communicated to a signaling device, for example a warning light, to alert an equipment operator, to a central maintenance facility to notify maintenance personnel when lubricant maintenance is needed, or to a signal processor that can convert the information to other output, for example a signal that can reduce the power output or turn "off" the equipment using the lubricant to prevent damage, or to a memory that can be downloaded when queried by, for example, a service technician's diagnostics system.

While FIG. 1 shows electrodes 3 of apparatus 1 in conduit 7 with flowing lubricant 5, apparatus 1 can be mounted in any location where lubricant 5 flows between electrode pairs 3 in a manner that allows the lubricant 5 between the electrodes 3 to be, at all times, maintained at a fixed temperature and representative of the current condition of the lubricant 5 in the equipment being monitored. For example, apparatus 1 can be mounted in a lubricant reservoir or sump where the heater 33 is located in close proximity to the electrodes 3 and the motion of lubricant 5 is sufficient to allow appropriate heating and relatively uniform mixing and exchange of lubricant within the equipment.

While FIG. 1 shows electrodes 3 to be flat rectangles with essentially only one surface of each electrode applying a signal from a signal generator to the lubricant between the electrodes, in another embodiment the electrodes can have other geometry including but not limited to, for example concentric-cylinders, flat with a multitude of finger-like sections, and an apparatus embodiment can have electrodes with multiple surfaces, surface sections, which may or may not directly face surface sections of the other electrode for applying a signal to the lubricant, interdigitated electrodes where finger-like sections of one electrode alternate with finger-like sections of the other electrode and the like.

While FIG. 1 shows one signal generator 11, one pair of electrodes 3 and one current sensor 15 to sequentially apply high and low frequency signals and measure high and low frequency lubricant responses, as is known in the art, multiple signal generator, electrode pairs and sensors can be used to apply signals and measure responses.

FIG. 1 shows apparatus 1 with no communication between temperature controller 29 and controller 17. In another embodiment the apparatus can have communication between the two controllers such that the method of this invention can use temperature information when determining lubricant condition or so that information about required lubricant temperature can be communicated to the temperature controller 29.

FIG. 1 shows apparatus 1 as individual components. In another embodiment apparatus 1 can integrate components into a compact package, which, for example reduces cost, size and/or power requirement of the apparatus. In another embodiment apparatus 1 can be incorporated into a package with other components, for example other lubricant sensors, that either can work in conjunction with or independent of the components of this invention.

FIG. 2 is a schematic illustration of another embodiment of the invention apparatus 43 that can be used to collect appropriate data. Apparatus 43 includes electrodes 3 immersed in lubricant 5 flowing in conduit 7. Electrodes 3 are fixedly held in and electrically isolated from conduit 7 by mount 9. Apparatus 43 also includes signal generator 11 for applying voltage signals of fixed amplitude and frequency through electrical conduits 13 to electrodes 3. One electrical conduit 13 of signal generator 11 is grounded for a voltage reference and the other conduit includes a current sensor 15 that measures electrical current flow through the conduit. Apparatus 43 includes thermocouple 31 immersed in lubricant 5 and fixedly held in conduit 7 by mount 35. Apparatus 43 further includes controller 17 with electrical conduit 19 for powering signal generator 11, electrical conduit 21 for monitoring output voltage of signal generator 11, electrical conduit 23 for monitoring current flow measured by current sensor 15, and electrical conduit 45 for monitoring the temperature of lubricant 5 measured by thermocouple 31. Controller 17 also has electrical conduit 25 to receive power and electrical conduit 27 to communicate information. Unlike apparatus 1 of FIG. 1, apparatus 43 does not include means for maintaining the temperature of lubricant 5.

In operation, lubricant 5 flows through conduit 7 and between electrodes 3, power is applied to controller 17 through electrical conduit 25. When used with a method of this invention, the method determines when controller 17 powers signal generator 11 to apply signals through conduits 13 and electrodes 3 to fluid 5. The electrical response of lubricant 5 to applied signals causes current to flow and to be measured by current sensor 15. Controller 17 monitors the applied signals and the corresponding current flows through electrical conduits 19, 21 respectively and compares magnitude and phase of the voltage and current signals to calculate electrochemical impedance of lubricant 5. Controller 17 also monitors thermocouple 31 through electrical conduit 45 to determine temperature of lubricant 5. The method of this invention uses the impedance data to determine condition of lubricant 5. Controller 17 can receive information that may be useful in a method embodiment through electrical conduit 27, for example, information that a volume of fresh lubricant was made or that an essentially complete lubricant exchange has occurred, or updates of values or functions used in the lubricant condition determination can be received. A method of this invention communicates information about the lubricant condition determination from controller 17 through electrical conduit 27 as described for apparatus 1 of FIG. 1.

In another embodiment, apparatus 43 of FIG. 2 can be mounted in locations other than conduit 7 as long as lubricant 5 flows between electrode 3 in a manner that allows the lubricant 5 between the electrode pairs to be at the temperature measured by thermocouple 31 and representative of the current condition of the lubricant 5 in the equipment being monitored. The electrodes 3 need not be flat plates with only one surface of each electrode opposed to the other electrode. In another embodiment the apparatus can have electrode geometries with greater than one surface of each electrode opposed to the other electrode. Apparatus 43 can be individual components, as shown in FIG. 2, or can be integrated components or integrated with components other than those of apparatus 43, which, for example, reduce cost, size and/or power requirements of the apparatus.

While apparatus 1 of FIG. 1 has a means for controlling the temperature of lubricant 5 and apparatus 43 of FIG. 2 has a means for determining the temperature of lubricant 5, in applications where the average lubricant temperature is relatively constant, preferably varying less than 5° C., more preferably varying less than 2° C., and most preferably varying less than 1° C., an apparatus similar to apparatus 43 of FIG. 2 but without thermocouple 31 and where controller 17 does not monitor the temperature of lubricant 5 as electrodes 3 apply a signal to the lubricant can be used with another embodiment of the method of the present invention.

FIG. 5 shows the ratio of the high frequency permittivity to initial high-frequency permittivity ($\epsilon/\epsilon_i$) as a function of mileage of a particular vehicle/engine for a typical standard-grade heavy-duty diesel engine lubricant where there was no fuel dilution 55, approximately 2% fuel dilution 57, approximately 4% fuel dilution 59 and approximately 6% fuel dilution 61 at about 12,000 miles. The initial high-frequency permittivity $\epsilon_i$ is the permittivity of fresh, that is unused, lubricant. Dashed lines 63 and 65, as will be more fully explained below, mark the error limits of no fuel dilution high-frequency $\epsilon/\epsilon_i$ curve 55 that are expected as a function of mileage. Mileage is the distance driven since the last oil change and is a measure of engine oil use. Permittivity ratios 55, 57, 59 and 61 were determined from temperature corrected engine oil response to an about 500 kHz essentially sinusoidal voltage signal applied to electrodes with an area to gap ratio of about 50 cm. For curves 57, 59 and 61 fuel was added to the lubricant as a linear function of mileage such that there was no fuel in the lubricant at zero mileage and approximately half the amount of fuel at about 6,000 miles and the full amount of fuel at about 12,000 miles.

The $\epsilon/\epsilon_i$ curve 55 of FIG. 5 is the average $\epsilon/\epsilon_i$ measured as a function of mileage for the particular vehicle/engine over the intended range of applications where there was no fuel dilution of the lubricant. The increase of curve 55 as a function of use is consistent with the increase with the soot content of the lubricant as is described in U.S. patent application Ser. No. 10/841,757 entitled "Method for On line Monitoring Condition of Non Aqueous Fluids" filed May 7, 2004. Dashed lines 63, 65 represent the $\epsilon/\epsilon_i$ variation from the average curve 55 that occur due to variations in lubricants, fuels, vehicle operating conditions, engine condition, and other variables that affect the $\epsilon/\epsilon_i$ ratio. The no fuel dilution $\epsilon/\epsilon_i$ curve 55 could also be an extrapolation of the $\epsilon/\epsilon_i$ data at near zero mileage where fuel dilution is assumed to be approximately zero. That is, even if the vehicle/engine has a fuel dilution problem, after a lubricant change, even with some residual lubricant remaining in the engine, the initial rise of $\epsilon/\epsilon_i$ can be assumed to be due to effects other than fuel dilution because of the low fuel dilution, and no-fuel dilution curve 55 can be an extrapolation of the initial rise. Dashed lines 63, 65 would then represent the error limits of the extrapolation assumptions and variations in fuels and operating conditions that may affect the $\epsilon/\epsilon_i$ ratio after the initial increase. A curve 55 based on an extrapolation of initial $\epsilon/\epsilon_i$ increase can minimize the effect of variations due to different lubricants and due to engine condition as the engine ages, but has increased error based on the ability to estimate the initial $\epsilon/\epsilon_i$ increase as a function of use due to variables, for example system noise, that affect the short term $\epsilon/\epsilon_i$ signal. In either case, the $\epsilon/\epsilon_i$ is expected to fall within the range bounded by dashed lines 63, 65 as a function of lubricant use. Therefore, knowing the lubricant use, curve 55 can be used to predict $\epsilon/\epsilon_i$ or changes of $\epsilon/\epsilon_i$ as a function of lubricant use within the bounds of lines 63, 65. The separation between lines 63, 65 varies depending on engine and application, and can be dependent on the selected lubricant use-measure selected for the X-axis. Mileage, as used in FIG. 5, is a convenient lubricant use-measure for many applications. Equipment operation time, that is the length of time that the equipment is "on", is another convenient lubricant use-measure. However, in applications where the lubricated equipment is operated over a wide range of speeds and loadings and/or where lubricant temperature can vary over a wide range, the permittivity-ratio increase as a function of mileage or operation time can have relatively wide variation and a more accurate lubricant use-measure may be needed. Depending on equipment and application, an appropriate lubricant use-measure may be a function that includes one or more equipment use-measures such as operating time, energy output, distance traveled, number of operating cycles, operating temperature, fuel consumption, start/stop cycles, etc. since the last lubricant change, or a lubricant use-measure may include measured lubricant properties such as infrared absorption, or electrical response properties at frequencies other than those used by this invention. As an example, U.S. Pat. No. 4,742,476 to Schwartz et al. describes a method for estimating lubricant use that may be appropriate for producing a relatively accurate use estimate. In any case, the permittivity-increase band for the selected lubricant use-measure must be sufficiently small to allow a relatively accurate approximation of the fuel dilution in lubricant.

Referring to FIG. 5, curves 57, 59, 61 of the fuel-containing samples are lower than the no-fuel curve 55 with the difference between the no-fuel and the fuel-containing curves increasing with both fuel amount and mileage, that is, lubricant use. Comparison of the actual $\epsilon/\epsilon_i$ of fuel-containing curves 57, 59, 61 to a predicted no-fuel $\epsilon/\epsilon_i$ based on the boundaries 63, 65 allows an approximation, that is an estimate, of the fuel content of the lubricant being monitored. The ratio of actual $\epsilon/\epsilon_i$ to a predicted no-fuel $\epsilon/\epsilon_i$ as a function of lubricant use is of benefit in estimating fuel content. The difference between the slope and/or the curvature actual $\epsilon/\epsilon_i$ as a function of lubricant use and a predicted slope and/or curvature no-fuel $\epsilon/\epsilon_i$ as a function of lubricant use can also be used to estimate fuel content. An issue with comparing a change, for example a slope or a curvature, in an actual $\epsilon/\epsilon_i$ change to a predicted change as a function of use is that if the high-frequency lubricant response has significant noise, that is variability, additional data averaging or smoothing is needed to allow for reliable measurement of change, which may cause a time-lag in the lubricant condition determination. Hence, the ratio of actual-to-predicted $\epsilon/\epsilon_i$ as a function of lubricant use is a preferred method for estimating fuel content in a lubricant.

While the no-fuel curve 55 of FIG. 5 is shown where linearly increasing as a function of use, the no-fuel curve need not be linear as a function of use either as an average of actual $\epsilon/\epsilon_i$ data or as an extrapolation of $\epsilon/\epsilon_i$ data at near zero lubricant use. Similarly fuel-containing $\epsilon/\epsilon_i$ curves need not have the shape shown by curves 57, 59, 61 of FIG. 5.

Figure 6:
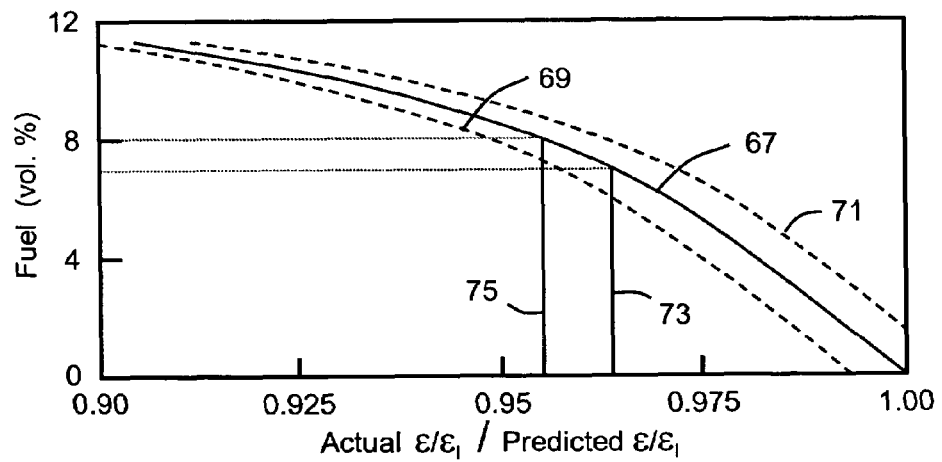
FIG. 6 is a graphic representation of the percentage of fuel as a function of the ratio of high-frequency actual $\epsilon/\epsilon_i$ to predicted no-fuel $\epsilon/\epsilon_i$ for diesel engine oils.

FIG. 6 represents an example of the laboratory-determined fuel content versus the ratio of actual-to-predicted $\epsilon/\epsilon_i$ for several different diesel-powered vehicles operated in similar applications using a variety of engine lubricants. The predicted values for $\epsilon/\epsilon_i$ are no-fuel values of FIG. 5. Curve 67 is the best fit second-order curve for the data, and dashed lines 69 and 71 approximate the error range associated with boundaries 63, 65 of FIG. 5. With continued reference to FIG. 6, estimates for fuel concentrations below about 2% are not meaningful because of error curves 69, 71. A more accurate lubricant use-measure may allow meaningful fuel estimates below about 2%. A less accurate lubricant use-measure would probably have a lower limit for meaningful estimates of greater than about 2%. In any case, if the actual-to-predicted $\epsilon/\epsilon_i$ is outside the lower limit for meaningful fuel estimate, a method of this invention can provide an output that fuel dilution is occurring. An output can also be provided that is an estimate, or approximation, of the fuel concentration in the lubricant. Most engine manufacturers have thresholds for the maximum fuel dilution allowed, for example, a manufacturer may have an 8% fuel condemnation limit. Shown in FIG. 6 are threshold 73, 75 where curve 67 corresponds to about 7% and about 8% fuel content respectively. A method of this invention can provide output, for example a signal to "change oil soon", when the actual-to-predicted $\epsilon/\epsilon_i$ is below threshold 73 and can provide another output, for example "change oil now", when the actual-to-predicted $\epsilon/\epsilon_i$ is below threshold 75. Obviously, the thresholds 73, 75 can be set more conservatively based on the possible error limit 71 to assure that the an engine is protected from ever exceeding about an 8% concentration, or whatever concentration an engine manufacturer desires, so long as the condemnation limit is above the method's lower limit for a meaningful fuel content estimate. Obviously, only one threshold or more than two thresholds, or a continuous output that is a function of determined fuel content can be used to meet manufacturer or end-user needs when determining the condition of a lubricant.

Figure 7:
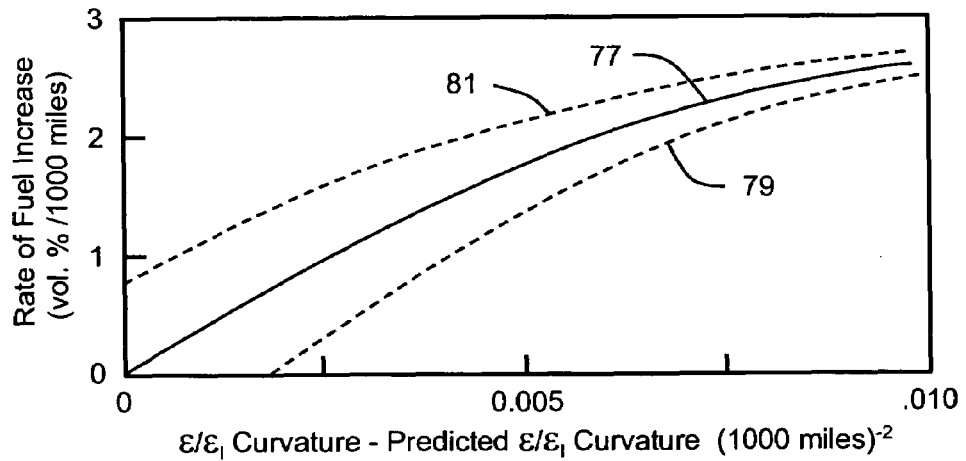
FIG. 7 is a graphic representation of the percentage fuel as a function of the curvature of the high-frequency $\epsilon/\epsilon_i$ with use for diesel engine oils.

FIG. 7 shows an example of how the difference between an actual change of $\epsilon/\epsilon_i$ and predicted change of $\epsilon/\epsilon_i$ as a function of lubricant use can be used to estimated fuel content. The graphical representation shows the rate of fuel increase in the lubricant as a function of difference between actual $\epsilon/\epsilon_i$ curvature [$\delta^2(\epsilon/\epsilon_i)/\delta(\text{lubricant use})^2$] and predicted no-fuel $\epsilon/\epsilon_i$ curvature. Curve 77 is a best fit curve using the data of FIG. 6, and dashed lines 79 and 81 are error limits associated with boundaries for the predicted values using curves 63, 65 of FIG. 5 and the error associated with determining the curvature of the actual $\epsilon/\epsilon_i$ which increases substantially as curvature decreases. Fuel content in a lubricant is determined as follows, the average $\epsilon/\epsilon_i$ curvature is determined for incremental periods of lubricant-use starting from when the lubricant is fresh, for each incremental period the fuel increase is the product of the average rate of fuel increase determined using the average curvature and curve 77 of FIG. 7 times the lubricant-use during the period, and sum of the incremental increases is the total fuel concentration. The determined total fuel concentration can then be compared to fuel dilution condemnation or warning thresholds to determine the condition of the lubricant. Because of the high error limits, especially for small curvatures, this method typically has greater error when estimating fuel concentration when compared to the preferred fuel estimation method of FIG. 6.

While FIG. 7 is shown and described using the curvatures of the actual and predicted $\epsilon/\epsilon_i$ as the change in $\epsilon/\epsilon_i$ that can be used to determine lubricant fuel-content condition. Although not shown, the rate of fuel increase can also be determined knowing the difference between the slopes of actual and predicted $\epsilon/\epsilon_i$ as a function of use. Knowing the fuel increase rate as a slope difference can be used for incremental lubricant-use periods starting when the lubricant is fresh to determine total fuel content in the fuel. This method, however also has typically greater error when estimating fuel concentration than the preferred fuel estimation method of FIG. 6.

While FIGS. 5, 6, 7 show $\epsilon/\epsilon_i$ for applications where there were no additions of fresh lubricant to maintain lubricant volume due to lubricant lost through consumption or leakage, the present invention is not limited to determine a lubricant fuel-condition for a lubricant where there are no additions of fresh lubricant to maintain lubricant volume between essentially complete lubricant changes.

Figure 8:
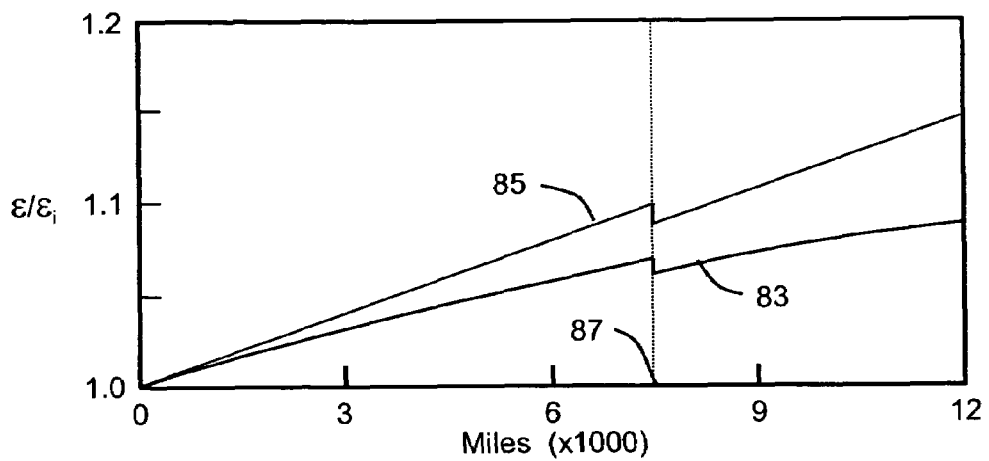
FIG. 8 is a graphic representation of the actual high-frequency $\epsilon/\epsilon_i$ to predicted no-fuel $\epsilon/\epsilon_i$ as a function of use where a volume of fresh lubricant is added during use to maintain lubricant volume.

FIG. 8 is a graphic representation of a high-frequency $\epsilon/\epsilon_i$ 83 for an engine lubricant where fuel dilution increases during lubricant use. Curve 85 is a predicted no-fuel $\epsilon/\epsilon_i$. The dotted line at use 87 marks where a volume of fresh lubricant, containing no fuel, is added to maintain lubricant level in the engine. The added lubricant causes a decrease in the high-frequency $\epsilon/\epsilon_i$ 83 due to both the reduced fuel concentration and the reduced average or effective use of the resulting lubricant volume that now contains a portion of fresh lubricant. If, for the fuel concentration method described with reference to FIG. 6, the predicted $\epsilon/\epsilon_i$ 85 were not corrected at use 87, the ratio of actual-to-predicted $\epsilon/\epsilon_i$ would show a step decrease such that a fuel concentration estimate using, for example, curve 67 of FIG. 6, would show a step increase instead of the decrease that is expected with the fresh lubricant addition. Hence, the predicted $\epsilon/\epsilon_i$ should be compensated to better estimate the resulting fuel concentration after the fresh lubricant addition. The method selected to compensate the predicted $\epsilon/\epsilon_i$ of FIG. 8 assumed that the actual $\epsilon/\epsilon_i$ change of the resulting lubricant volume is due equally to reduced use and to reduced fuel concentration. That is, the use-measure after fresh lubricant addition is reduced such that the percentage change in use-measure results in the same percentage change in fuel-concentration estimate. Referring to FIG. 8, before the fresh fluid addition, the actual/predicted $\epsilon/\epsilon_i$ estimated that the fuel content was 6.3%, after the addition a calculation showed that reducing the predicted $\epsilon/\epsilon_i$ 16% resulted in a equal 16% decrease in the fuel content to 5.3%. Hence, after use 87, the use-measure "t" is reduced by an amount needed to reduce the predicted $\epsilon/\epsilon_i$ 16% at use 87 as shown by curve 85.

While FIG. 8 used one method to reduce the predicted $\epsilon/\epsilon_i$ with a fresh lubricant addition, other methods can be used within the scope of this invention. For example, another method would offset the use-measure for use above 87 by an amount such that the ratio of actual/predicted $\epsilon/\epsilon_i$ is the same after the fresh lubricant addition as before the addition. Keeping the ratio of actual-to-predicted $\epsilon/\epsilon$ the same before and after the fresh lubricant addition results in the after-addition fuel concentration estimate being the same as the before estimate, which typically overestimates the amount of fuel in the lubricant volume after the fresh lubricant addition.

While FIG. 8 is shown and described for use with a method of fuel dilution estimation described with reference to FIG. 6, the incremental change in actual $\epsilon/\epsilon_i$ shown by curve 83 at use 87 of FIG. 8 could be use with the fuel concentration method described with reference to FIG. 7. For the method of FIG. 7, the change in actual $\epsilon/\epsilon_i$ could be used to offset the total fuel concentration which is the sum of the fuel concentration increases for incremental use periods up to use 87. For example, fuel concentration after use 87 could be offset by the same percent as the offset in $\epsilon/\epsilon_i$ 83 at use 87. That is, if $\epsilon/\epsilon_i$ decreases "Y%" than the total fuel concentration is reduced "Y%" at use 87 and this becomes the new staring point for adding fuel concentration increases that occur for incremental use periods after use 87.

While not shown in FIG. 8, a complete replacement of used lubricant with fresh lubricant would result in a large change in $\epsilon/\epsilon_i$, with the value returning to approximately 1 since the initial high-frequency permittivity of most diesel lubricants falls typically within a relatively narrow range. Hence, a large permittivity change that returns the $\epsilon/\epsilon_i$, to approximately 1 can be interpreted as an essentially complete lubricant change and $\epsilon_i$ can be reset and the use-measure set to zero so as to begin monitoring the fuel-dilution condition of the replacement lubricant.

Figure 9:
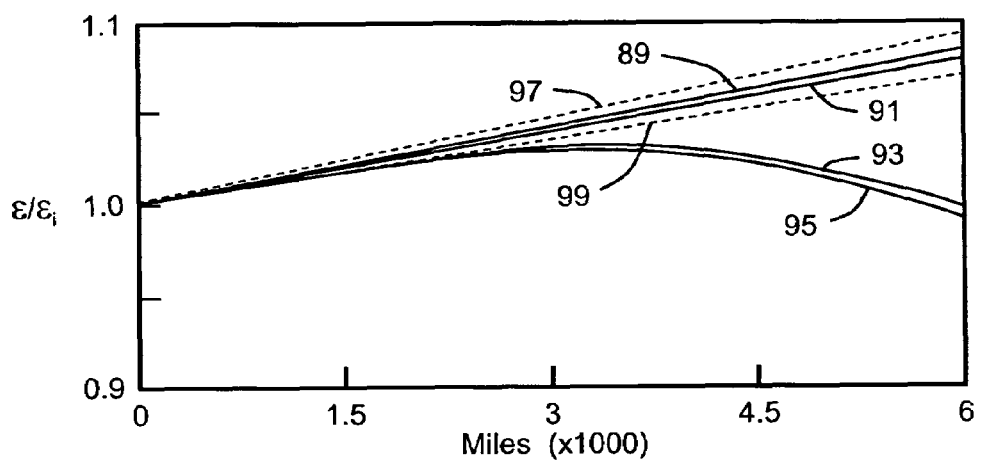
FIG. 9 is a graphic representation of the high-frequency $\epsilon/\epsilon_i$ of two gasoline engine oils with increasing fuel dilution and with no fuel dilution as a function of engine use.

Shown in FIG. 9 are high-frequency $\epsilon/\epsilon_i$ as a function of mileage in a particular gasoline engine powered vehicle for no fuel dilution 89, 91 and approximately 6% fuel dilution 93, 95, for two lubricants, A and B respectively, at about 6,000 miles. The high-frequency permittivity ratios $\epsilon/\epsilon_i$ 89, 91, 93, 95 were determined from temperature corrected engine oil response to about a 500 kHz essentially sinusoidal voltage signal applied to electrodes with an area to gap ratio of about 50 cm. For curves 93 and 95 fuel was added to the lubricant as a linear function of mileage such that there was no fuel in the lubricants at zero mileage and approximately half the amount of fuel at about 3,000 miles and the full amount of fuel at about 6,000 miles. Also shown in FIG. 9 are dashed lines 97, 99, which indicate the typical range of no-fuel $\epsilon/\epsilon_i$ that is expected for a lubricant as a function of mileage in this vehicle engine.

Referring to FIG. 9, the no-fuel $\epsilon/\epsilon_i$ curves 89, 91, for gasoline engine lubricants A and B respectively, show about the same relatively small increase as a function of mileage, and that the typical range for the $\epsilon/\epsilon_i$ increase is relatively small as marked by dashed curves 97, 99. In some applications, the no fuel $\epsilon/\epsilon_i$ has essentially zero change as a function of use such that the predicted $\epsilon/\epsilon_i$ and can be assumed to be fixed independent of use. Fuel diluted lubricant $\epsilon/\epsilon_i$ curves 91, 93 of lubricants A and B respectively show about the same change of $\epsilon/\epsilon_i$ relative to the respective no-fuel curves 89, 91. That is, increasing fuel content as a function of mileage affects $\epsilon/\epsilon_i$ about equally for the two lubricants.

Figure 10:
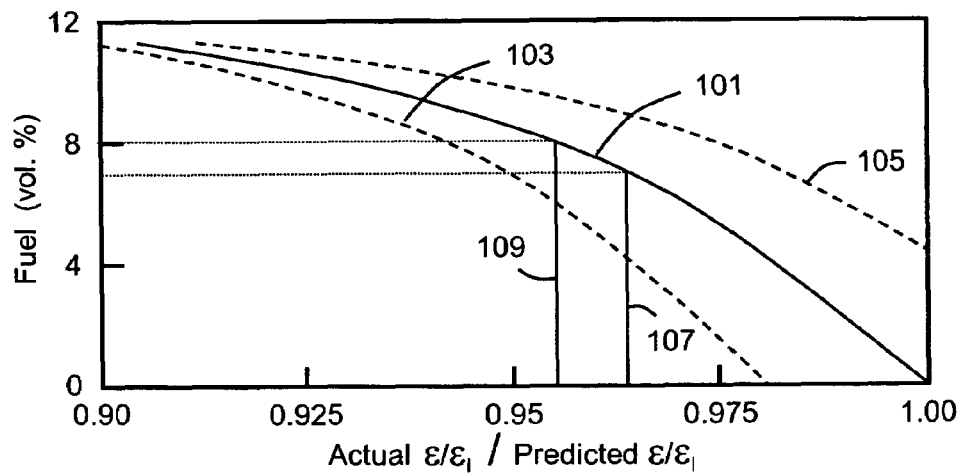
FIG. 10 is a graphic representation of the percentage fuel as a function of the high-frequency actual $\epsilon/\epsilon_i$ to predicted no-fuel $\epsilon/\epsilon_i$ for gasoline engine oils.

FIG. 10 represents an example of the laboratory determined fuel content versus the ratio of actual-to-predicted $\epsilon/\epsilon_i$ for several different gasoline-powered vehicles operated in similar applications using a variety of engine lubricants. The predicted values for $\epsilon/\epsilon_i$ are based on mileage. Curve 101 is the best fit second-order curve, and dashed lines 103 and 105 approximate an error range due to limits of the predicted $\epsilon/\epsilon_i$, for example, the no-fuel permittivity range shown by lines 97, 99 of FIG. 9. Curve 101 can be used to estimate fuel concentration. The accuracy of the estimate is determined by the error limits of curves 103, 105. For FIG. 10, estimates for fuel concentrations below about 5% are not meaningful due to the error limits. As with the diesel lubricant, a more accurate lubricant use-measure may reduce the error range, although gasoline engine lubricants typically show quite small change in $\epsilon/\epsilon_i$ for the first several percent of fuel concentration thereby making fuel concentration estimates below about 2 to about 3% difficult even with a more accurate lubricant use-measure. In any case, if the actual-to-predicted $\epsilon/\epsilon_i$ is outside the lower limit for meaningful fuel estimate, a method of this invention can provide an output that fuel dilution of the lubricant is occurring. An output can also be provided that is an estimate, or approximation, of the fuel concentration in the lubricant. Threshold, for example as shown by lines 107, 109, can be used consistent with engine manufacture fuel-dilution condemnation limits to provide output, for example a signal to "change oil soon", when the actual-to-predicted $\epsilon/\epsilon_i$ is below threshold 107, and/or a signal to "change oil now", when the actual-to-predicted $\epsilon/\epsilon_i$ is below threshold 109.

A figure similar to FIG. 7 could also be drawn for the gasoline lubricants of FIG. 10. Error limits of such a figure, however, are very large limiting the usefulness of such a curve in fuel concentration estimates.

Figure 11:
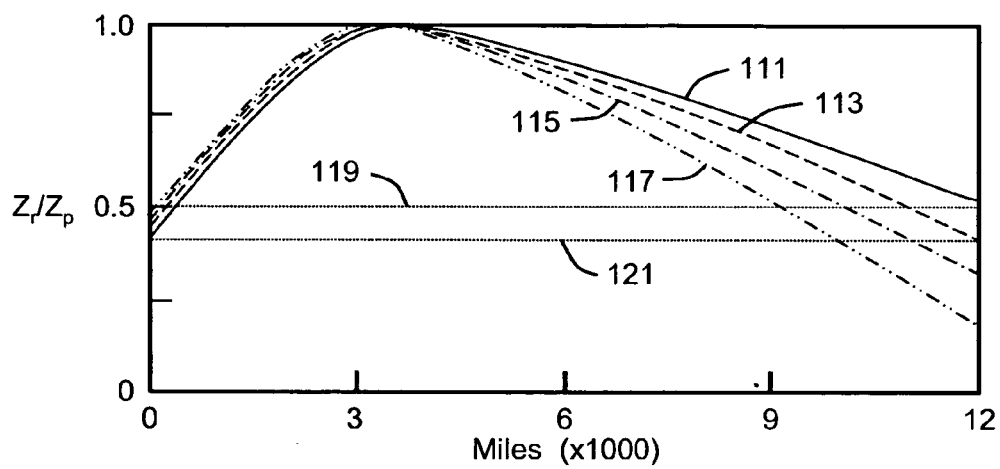
FIG. 11 is a graphic representation of the low-frequency real impedance ratio, that is, measured real impedance divided by the peak real impedance measured during use $Z_r/Z_p$, of a diesel engine oil with increasing fuel dilution and with no fuel dilution as a function of engine use.

FIG. 11 shows the ratio of the low-frequency real impedance to the peak low-frequency real impedance $Z_r/Z_p$ versus vehicle mileage, for the same heavy-duty diesel lubricants of FIG. 5, where there is no fuel dilution 111, approximately 2% fuel dilution 113, approximately 4% fuel dilution 115 and approximately 6% fuel dilution 117 at about 12,000 miles of use. Curves 111, 113,115, 117 were determined from temperature corrected oil response to a 100 Hz essentially sinusoidal voltage signal applied to electrodes with an area to gap ration of about 50 cm. For curves 113, 115, 117, fuel was added to the lubricant as a linear function of mileage such that there was no fuel in the lubricant at zero mileage and approximately half the amount of fuel at about 6,000 miles and the full amount of fuel at about 12,000 miles. As taught in previously cited U.S. application Ser. No. 10/271,885, Lvovich et al., a lubricant's $Z_r$ (which for many lubricants is essentially the same as total impedance |Z|) at what is described therein as a medium frequency, which is the same as the low frequency herein, typically shows a rise to $Z_p$ followed by a decrease as a function of use. The Lvovich et al. method further teaches that the rate of decrease of $Z_r/Z_p$ for different lubricants in the same application can vary as function of the quality of the lubricant, and that lubricant condition can be determined by comparing the ratio of measured $Z_r/Z_p$ to one or more thresholds. Referring to FIG. 11, the starting points and peaks of curves 111, 113, 115, 117 vary slightly due to a fuel induced shift in peak location and value for each curve. However, the curves 111, 113, 115, 117 show that after the peak, $Z_r/Z_p$ decreases more rapidly and therefore more rapidly reach thresholds 119 and 121 with increasing fuel concentration. The use of the low frequency $Z_r/Z_p$ thresholds provides information in addition to the high frequency fuel content estimate when determining a lubricant's fuel-dilution condition is described with reference to FIG. 12.

Figure 12:
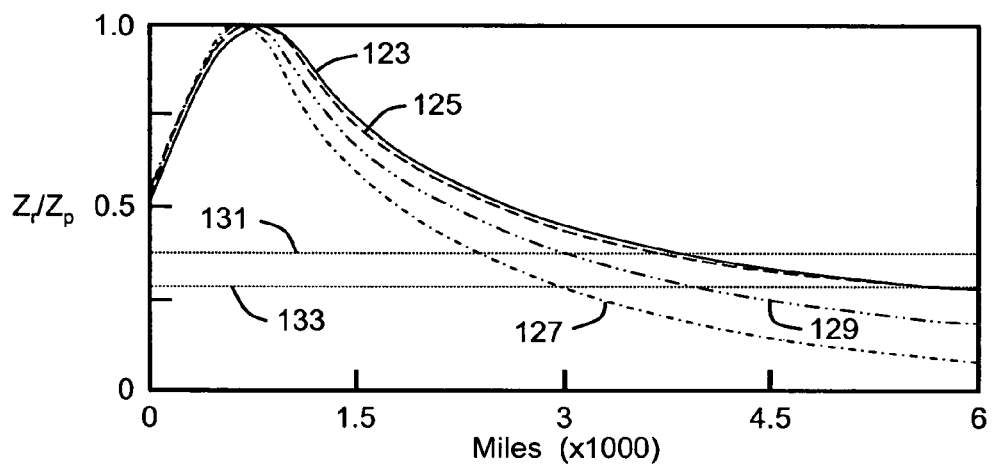
FIG. 12 is a graphic representation of the low-frequency $Z_r/Z_p$ of two gasoline engine oils with increasing fuel dilution and with no fuel dilution as a function of engine use

FIG. 12 shows $Z_r/Z_p$ as a function of vehicle mileage for gasoline engine lubricants A and B of FIG. 9, where there is no fuel 123 and 125 respectively and approximately 6% fuel dilution 127 and 129 respectively at about 6,000 miles of use. Curves 123, 125, 127, 129 were determined from temperature corrected oil response to a 100 Hz essentially sinusoidal voltage signal applied to electrodes with an area to gap ration of about 50 cm. For curves 127 and 129 fuel was added to the lubricant as a linear function of mileage such that there was no fuel in the lubricant at zero mileage and approximately half the amount of fuel at about 3,000 miles and the full amount of fuel at about 6,000 miles. Curves 123 and 125 show similar decreases after their peak $Z_r/Z_p$ and each reaches thresholds 131 and 133, which are set consistent with the previous teachings of Lvovich et al., after approximately the same amount of use. That is, with no fuel dilution both oils are of similar quality as determined by the low frequency response. Curves 127 and 129, however, show quite different decrease after their peak $Z_r/Z_p$. Curve 127 decreases more rapidly and reaches thresholds 131 and 133 after less use than curve 129. In particular, lubricant A reaches the "change oil now" threshold 133 at about 3,000 miles with about 3% fuel dilution, and lubricant B reaches threshold 133 at about 4,000 miles with about 4% fuel dilution. That is, the condition of lubricant B is less affected by fuel dilution than the condition of lubricant A, and therefore, as defined herein, lubricant B controls the fuel dilution better than lubricant A. There is also evidence that the type of fuel, for example a bio-fuel versus an essentially all petroleum fuel, can influence how well a particular lubricant can control fuel dilution. Hence, while high frequency $\epsilon/\epsilon_i$ for lubricants A and B can be used to determine the amount of fuel in lubricants A and B, that information alone may not be sufficient to determine when to change a lubricant unless a %-fuel condemnation threshold is set sufficiently low to assure that both lubricants do not first reach end-of-life due to the lubricant condition measured by low-frequency $Z_r/Z_p$. In the case of lubricant A, a %-fuel condemnation threshold would have to be set below about 3%, or possibly lower depending on the type of fuel, to adequately protect the engine.

In addition to protecting against lubricants that are adversely affected by fuel dilution, the low-frequency $Z_r/Z_p$ allows a determination if a substantial change in the responses is due to an addition of fresh lubricant or due to a sudden rapid addition of fuel to the lubricant as will now be shown.

Figure 13:
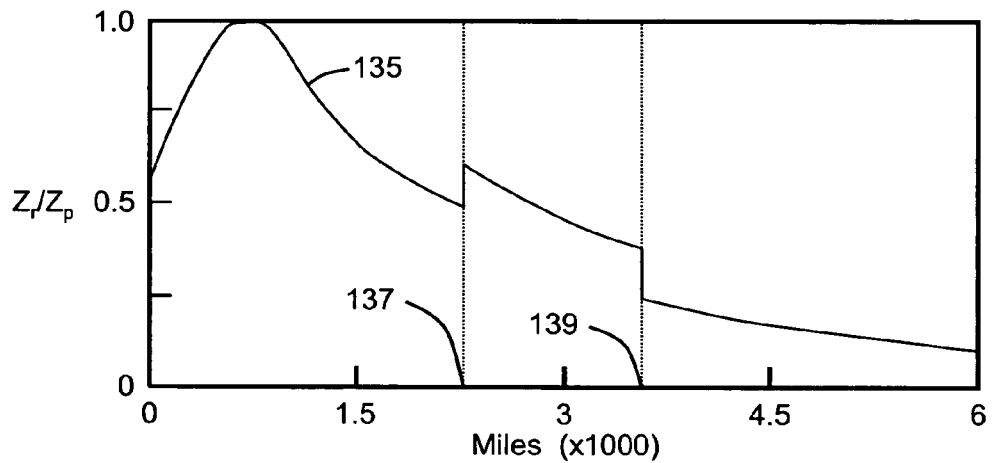
FIG. 13 is a graphic representation of the low-frequency $Z_r/Z_p$ of a gasoline engine oil where a volume of fresh oil is added to the lubricant during use and where a volume of fuel is incrementally added to the lubricant during use.

FIG. 13 is a graphic illustration that shows $Z_r/Z_p$ 135 as a function of vehicle mileage for a gasoline engine lubricant where fresh lubricant was added to maintain lubricant volume at use 137 and a quantity of fuel was incrementally added to the lubricant at use 139. The addition of fresh lubricant at 137 results in a $Z_r/Z_p$ increase, whereas the sudden addition of fuel at 139 results in a $Z_r/Z_p$ decrease. Although not shown a complete lubricant change can result in either a $Z_r$ increase of or decrease, but has the further property that after a complete lubricant replacement the $Z_r$ does not decrease, and typically rises. Hence, when combined with measured changes in the lubricant high-frequency response, the low-frequency response can be used to distinguish between fresh lubricant additions, fuel additions and complete lubricant changes.

Figure 14:
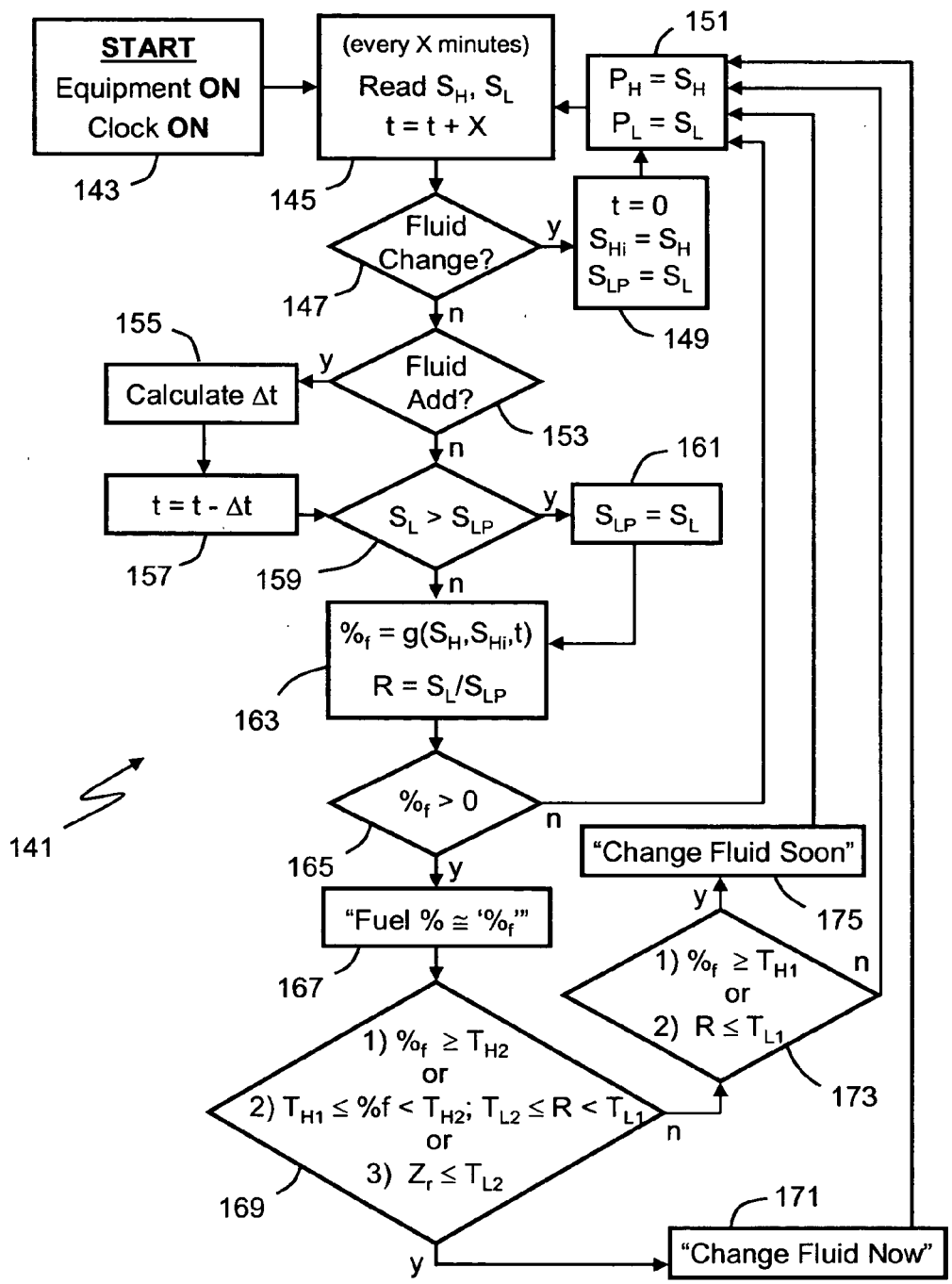
FIG. 14 is a flow chart of a feature of the present invention wherein high-frequency permittivity response data and low-frequency real impedance data are used to determine and output lubricant condition.

FIG. 14 shows a method embodiment 141 of a feature of the present invention that uses above described high frequency permittivity method of FIGS. 6, 8 and 10, and low frequency real impedance method of FIGS. 11 and 12 to determine the fuel-dilution condition of an engine oil where the oil is maintained at a relatively constant temperature for condition determination. The temperature can be maintained either by the measurement apparatus, for example apparatus 1 in FIG. 1, or by the engine or a means associated with the engine in which the lubricant is used.

Referring to FIG. 14, method 141 begins in block 143 where each time the equipment is turned "on", i.e. started, a clock that outputs time is also turned "on". In this embodiment time is lubricant use-measure. After start-up, method 141 proceeds to block 143 to read lubricant response $S_H$ to an applied high-frequency signal and lubricant response $S_L$ to an applied low-frequency signal. Signals $S_H$ and $S_L$ are obtained by a measurement apparatus of the type described in association with FIG. 1. $S_H$ can be a permittivity value as used in FIGS. 5, 6, 7, 8, 9, 10 or a value that is essentially equivalent. $S_L$ can be a real impedance value as used in FIGS. 11, 12, 13 or a value that is essentially equivalent. For example, instead of converting the lubricant responses $S_H$, $S_L$ to values with appropriate dimensional units, analogue voltages, currents or digital inputs can be read that can be converted to appropriate lubricant responses. As another example, the responses may be received as total impedance and phase angle signals. As another example, in applications where the low-frequency imaginary impedance is substantially smaller than the real impedance, the real impedance can be approximated by the total impedance such that $S_L$ can be the total impedance. $S_H$ and $S_L$ can be data collected by the apparatus over a short period of time with no filtering, or can be averaged over a longer period of time and filtered to minimize noise and to better quantify the lubricant's response. In any case, while the equipment is "on" the method reads $S_H$ and $S_L$ in block 145 at fixed intervals of "X" minutes and lubricant use-measure "t" is increased by X each time $S_H$, $S_L$ are read.

After inputs $S_H$, $S_L$ are read, method 141 in block 147 determines if an essentially complete lubricant change occurred since the last time $S_H$, $S_L$ were read. This determination can be based on an input to the method. For example, a maintenance person, or operator, could provide a signal when a lubricant change is made that is communicated to the controller (e.g. by electrical conduit 27 to controller 17 of apparatus 1 in FIG. 1) and detected in block 147. As another example, a sensor or sensor system that detects lubricant change either by a lubricant level change or by other means could provide a signal that is detected in block 147. The determination of block 147 can also be made comparing inputs $S_H$, $S_L$ to previous $S_H$, $S_L$ ($P_H$, $P_L$ respectively) inputs and/or expected initial values of $S_H$, $S_L$ with no additional input to method 141 needed. If the determination in block 147 is "yes", then in block 149 initial value $S_{Hi}$ for the high-frequency signal determination (corresponding to the initial permittivity $\epsilon_i$ value of FIGS. 5, 6, 7, 8, 9, 10) is set equal to $S_H$, the peak value $S_{LP}$ for the low-frequency signal determination (ultimately corresponding to the peak real impedance $Z_P$ value of FIGS. 11, 12, 13) is set equal to $S_L$, and the use-measure "t" is set equal to zero indicating that the fresh lubricant has zero use when first added to the equipment. Method 141 then proceeds to block 151 where the previous high-frequency response $P_H$ is set equal to $S_H$, and the previous low-frequency response $P_L$ is set equal to $S_L$ and the method 141 returns to block 145 to again read $S_H$ and $S_L$ X minutes after the values that are now $P_H$, $P_L$ were read and to increase "t" by X minutes.

If the determination in block 147 is "no", method 141 advances to block 153 to determine if a partial addition of fresh lubricant occurred since the last time $S_H$, $S_L$ were read. This determination can be based on an input to the method as described by the examples above, or can be based on comparison to the $S_H$, $S_L$ to $P_H$, $P_L$ respectively. As previously explained, step changes in high-frequency permittivity as shown in FIG. 8 and in low-frequency real impedance as shown in FIG. 13 can be diagnosed as a fresh fluid addition. If the determination in block 153 is "yes", then in block 155 method 141 calculates a Δt to compensate, that is, to offset, the use-measure "t" as shown in block 157 such that the off-set "t" is more representative of the resulting lubricant use with the fresh fluid addition. The Δt calculated in block 155 can be based on an inputted or measured value of the amount of fresh lubricant added, or as previously discussed can be a number based on the step change in the $S_H$, $S_L$ values.

If the determination in block 153 is "no", or after the use-measure is offset by Δt in block 157, block 159 determines if $S_L$ is greater than the currently stored peak value $S_{LP}$. If the determination is "yes", then in block 161 $S_{LP}$ is replaced with $S_L$. In this manner, method 141 continues to increase $S_{LP}$ until an ultimate $S_{LP}$ is found. If the determination in block 159 is "no" or after block 161, a percent fuel dilution $\%_f$ or an equivalent is calculated in block 163 knowing the current $S_H$, the initial $S_{Hi}$, and the lubricant use-measure "t", as represented by the function $g(S_H, S_{Hi}, t)$. The calculation can be done using formulae, look-up tables or combinations thereof, such that the ratio $\epsilon/\epsilon_i$ or equivalent is compared to a predicted $\epsilon/\epsilon_i$ or predicted $\epsilon/\epsilon_i$ equivalent based on use-measure "t" to estimate the fuel concentration in the lubricant as described previously with reference to FIGS. 5, 6, 8, 9, 10. Also in block 163, the variable R is set equal to the ratio $S_L/S_{LP}$.

In block 165, the method 141 determines if fuel dilution $\%_f$ calculated in block 163 is greater than zero. If the determination is "no", then method 141 in block 151 resets the previous values $P_H$, $P_L$ and returns to block 145 to, X minutes after the previous reading, read $S_H$, $S_L$ and increase "t" by X minutes. If the determination of block 165 is "yes", then method 141 in block 167 sends a signal that the lubricant contains the estimated fuel concentration $\%_f$. The signal may be sent to memory for later retrieval, to a signaling device, for example a digital display, which can alert an equipment operator, to a central maintenance facility to notify maintenance personnel, to a signal processor that converts or uses the output in another output, for example to control the operation of the engine with the fuel diluted lubricant, or combinations thereof. After sending the signal, method 141 in block 169, determines if the estimated fuel concentration $\%_f$ is greater than or equal to a threshold $T_{H2}$, or if the real impedance ratio R is less than or equal to threshold $T_{L2}$, or if the estimated fuel concentration $\%_f$ is less than threshold $T_{H2}$ but greater than or equal to a threshold $T_{H1}$ and the real impedance ratio R is greater than threshold $T_{L2}$ but less than or equal to a threshold $T_{L1}$. That is, block 169 determines if the fuel dilution $\%_f$ is greater than a fuel condemnation threshold $T_{H2}$, for example threshold 81 of FIG. 7, if the real impedance ratio is less than the low frequency condemnation threshold $T_{L2}$, for example threshold 121 of FIG. 11, or if both the fuel dilution and the impedance ratio are between initial warning thresholds $T_{H1}$, $T_{L1}$ respectively, for example threshold 79 of FIG. 7 and threshold 119 of FIG. 11 respectively, and their condemnation thresholds. If the determination of block 169 is "yes", then method 141 in block 171 sends a signal that the lubricant has reached the end of its useful life and needs to be changed now. The warning may be sent to memory for later retrieval, to a signaling device, for example a warning light, which can alert an equipment operator, to a central maintenance facility to notify maintenance personnel, to a signal processor that, for example, controls the output of the equipment with the lubricant that has reached end-of-life, or combinations thereof. After sending the warning signal, method 141 resets the previous signals $P_H$, $P_L$ in block 151 and returns to block 145 to read $S_H$, $S_L$ and to increase "t" at the appropriate time. If the determination of block 169 is "no", a determination is made in block 173 whether $\%_f$ is greater than or equal to initial warning threshold $T_{H1}$, or the real impedance ratio R is less than or equal to initial warning threshold $T_{L1}$. If the determination is "yes", method 141 in block 175 sends a warning signal that the lubricant needs to be changed soon. If the determination block 173 is "no" then no warning message is send. In either case, after sending the signal in block 175 or after a "no" determination in block 173, method 141 resets the previous signals $P_H$, $P_L$ in block 151 and returns to block 145 to read $S_H$, $S_L$ and increase "t" at the appropriate time and begin the cycle again.

Method 141 continues to read $S_H$, $S_L$ and increase use-measure "t" every X minutes and to cycle through the blocks as described above while the equipment is "on". When the equipment is turned "off", the values of $P_H$, $P_L$, $S_{Hi}$, $S_{LP}$ and "t" remain in memory such that when the equipment is again turned "on", method 141 starts in block 143 and continues the cycle of stepping through the blocks to determine and, when necessary, give warnings about fuel concentration in the lubricant.

In this manner, method 141 essentially continuously monitors the fuel dilution of a lubricant and sends warnings based on the concentration of fuel in the lubricant and on the lubricant's ability to handle the fuel contained therein.

While the embodiment of FIG. 14 determines lubricant use with time "t" as the use-measure, as described previously, other use-measures can be used that are read or inputted to another embodiment.

While the embodiment of FIG. 14 uses the method to determine fuel concentration using the high-frequency $\epsilon/\epsilon_i$ as shown and described with reference to FIGS. 6 and 10, another embodiment could use the method of determining fuel concentration using the curvature of the high-frequency $\epsilon/\epsilon_i$ as shown and described with reference to FIG. 7. The embodiment could be similar to method 141 shown in FIG. 14, except: a) in blocks 155, 157 a $\Delta\%_f$ would be calculated and used to offset the fuel concentration respectively, b) in block 151 the two previous high-frequency lubricant responses $S_H$ would be saved as $P_{H1}$, $P_{H2}$, and c) in block 163 the function would be represented $g(S_H,S_{Hi},P_{H1},P_{H2},t)$ to indicate that at least two previous high-frequency responses are needed to calculate a $\epsilon/\epsilon_i$ curvature. In addition, the function "g" would determine fuel concentration by adding a fuel rate increase, found using the $\epsilon/\epsilon_i$ curvature, times the lubricant use interval X since the last determination.

While the embodiment of FIG. 14 uses a fixed $g(S_H,S_{Hi},t)$ that includes a fixed determination of a predicted $\epsilon/\epsilon_i$ or predicted $\epsilon/\epsilon_i$ equivalent as a function of use-measure "t", another embodiment could have a non-fixed $g(S_H,S_{Hi},t)$ that allows the determination of the predicted $\epsilon/\epsilon_i$ or predicted $\epsilon/\epsilon_i$ equivalent as a function of use-measure "t" to be updated each time the lubricant is changed such that the high frequency response from $t=0$ to $t=t_S$, where $t_S$ is a short use period during which the fuel dilution is assumed to be essentially zero, is used for the update as described with reference to FIG. 5.

While the embodiment of FIG. 14 reads and uses lubricant responses $S_H$, $S_L$ essentially immediately after the equipment is turned "on". In some applications there may be transients in the signal immediately after start-up, for example due to temperature variations or moisture condensation. In these applications, lubricant responses may not be meaningful for a fuel-dilution condition determination until the lubricant reaches steady-state. Hence, in another invention embodiment the method need not start making lubricant condition determination immediately on equipment start-up as long as the use-measure "t" properly reflects the appropriate lubricant use.

The embodiment of FIG. 14 sends a signal of the estimated amount of fuel dilution in block 169 in addition to warning signals to "change fluid soon" and to "change fluid now" in blocks 175, 171 respectively. Other embodiments can tailor the outputs to the needs of equipment operators and/or maintenance personnel consistent with the estimated fuel concentration $\%_f$, determine flow-frequency impedance ratio R. and lubricant use-measure "t". As an example, instead of having two thresholds for both $\%_f$ and the real impedance ratio R, other embodiments may independently have greater than or less than two thresholds to give warnings at different fuel concentrations and/or impedance ratios. As another example, an embodiment need not output the estimated fuel concentration, but may only provide output when thresholds are exceeded. As another example, instead of outputting the fuel concentration $\%_f$ or a warning that the lubricant needs to be changed soon, another embodiment may output an estimate on the remaining useful life of the lubricant or an estimate of the amount of use remaining before the lubricant needs to be changed, that replaced with fresh fluid, the current $\%_f$ and/or R and the condemnation thresholds $T_{H2}$ and $T_{L2}$ respectively.

The method of FIG. 14 uses both a lubricant's high-frequency response and low-frequency response to determine the fuel dilution condition of the lubricant based on an estimated concentration of fuel in the lubricant and the lubricant's ability to handle the fuel concentration. Assuming that any lubricant used in a particular application will be capable of handling fuel up to a set fuel condemnation limit, other embodiments can use only a lubricant's high-frequency response to determine the fuel dilution condition of the lubricant.

Figure 15:
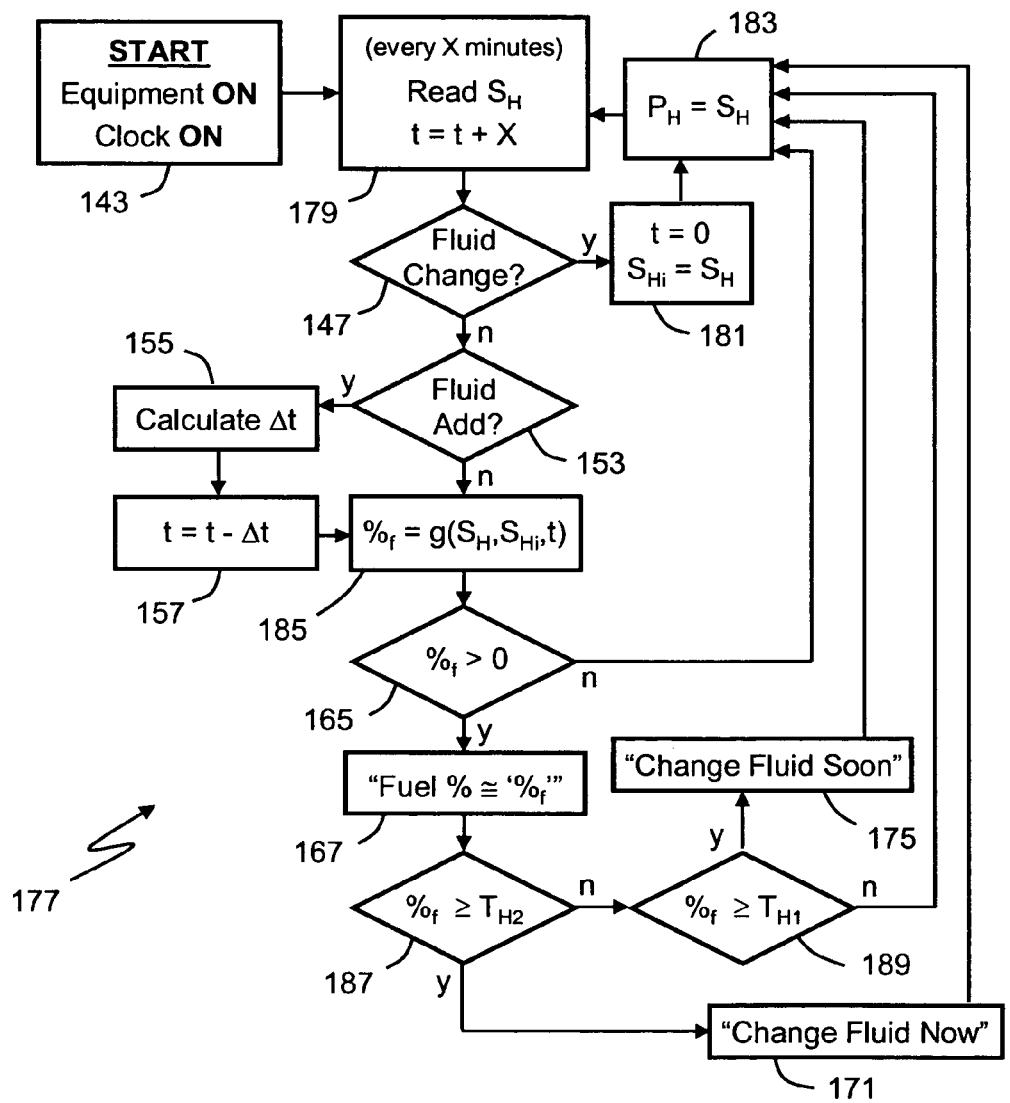
FIG. 15 is a flow chart of another feature of the present invention wherein high-frequency permittivity response data are used to determine and output lubricant condition.

FIG. 15 shows another embodiment 177 of a feature of the present invention for use in determining the condition of a lubricant in equipment where only the high-frequency response is use to determine a lubricant's fuel-dilution condition. To aid in describing the embodiment of FIG. 15, the blocks of method 177 that are the same as method 141 of FIG. 14 and are labeled the same.

Referring to FIG. 15, the method 177 begins in block 143 each time the equipment is turned "on" where a clock that outputs time is also turned "on". Time is the use-measure of this embodiment. After start-up method 179 proceeds to block 181 where only high frequency fluid response $S_H$ is read and use-measure "t" is increased by X. Proceeding to block 147, method 177 determines if an essentially complete fluid change occurred since the last time $S_H$ was read. This determination can be based on an input to the method or can be made comparing input $S_H$ to previous input $P_H$. If the determination in block 147 is "yes", then in block 181 the initial value $S_{Hi}$ for the high-frequency signal determination (corresponding to the initial permittivity $\epsilon_i$ value of FIGS. 5, 6, 7, 8, 9, 10) is set equal to $S_H$ and the use-measure "t" is set equal to zero indicating that the fresh lubricant has zero use when first added to the equipment. After which, in block 183 the previous high-frequency response $P_H$ is set equal to $S_H$, and the method 177 returns to block 179 to again read $S_H$, X minutes after the previous reading of $S_H$ was made, and to increase "t" by X minutes.

If the determination in block 147 is "no", method 177 advances to block 153 to determine if a partial addition of fresh lubricant occurred since the last time $S_H$ was read. This determination can be based on an input to the method on comparison to the $S_H$ to $P_H$. If the determination in block 153 is "yes", then in block 155 method 177 calculates a Δt to compensate of offset the use-measure "t" as shown in block 159 such that the offset "t" is more representative of the resulting lubricant with the fresh fluid addition. The Δt calculated in block 155 can be based on an inputted or measured value of the amount of fresh fluid added, or as previously discussed can be a number based on the step change in the $S_H$ value.

If the determination in block 153 is "no", or after the use-measure is offset by Δt in block 157, in block 185 a percent fuel dilution %$_f$ or an equivalent is calculated, knowing the current $S_H$, the initial $S_{Hi}$, and the lubricant use-measure "t", as represented by the function $g(S_H,S_{Hi},t)$. The calculation can be done using formulae, look-up tables or combinations thereof, such that the ratio $\epsilon/\epsilon_i$ or equivalent is compared to a predicted $\epsilon/\epsilon_i$ or equivalent based on use-measure "t" to estimate the fuel concentration in the lubricant as described previously with reference to FIGS. 5, 6, 8, 9, 10.

In block 165, the method 177 determines if fuel dilution %$_f$ calculated in block 185 is greater than zero. If the determination is "no", then method 177 in block 183 resets the previous values $P_H$ and returns to block 179 where X minutes after the previous reading $S_H$ is read and "t" is increased X minutes. If the determination of block 165 is "yes", then method 177 in block 167 sends a signal that the lubricant contains the estimated fuel concentration %$_f$. The signal may be sent to memory for later retrieval, to a signaling device, for example a digital display, which can alert an equipment operator, to a central maintenance facility to notify maintenance personnel, to a signal processor that can, for example, limit the equipment operation based on fuel content or operate a system that can modify a lubricant property, or combinations thereof. After sending the signal, method 177 determines, in block 187, if the estimated fuel concentration %$_f$ is greater than or equal to a threshold $T_{H2}$, which is the fuel condemnation threshold, for example threshold 75 of FIG. 6. If the determination of block 187 is "yes", then method 177 in block 171 sends a signal that the fluid has reached the end of its useful life and needs to be changed now, after which method 177 resets the previous signals $P_H$ in block 183 and returns to block 179 to again begin the steps of the method. If the determination of block 187 is "no", a determination is made in block 189 if %$_f$ is greater than or equal to initial warning threshold $T_{H1}$. If the determination is "yes", method 177 in block 175 sends a warning signal that the fluid needs to be changed soon. If the determination block 189 is "no" then no warning message is send. In either case, after sending the signal in block 175 or after a "no" determination in block 189, method 177 resets the previous signals $P_H$, in block 185 and returns to block 179 to again read $S_H$, increase "t" at the appropriate time and begin the cycle again.

Method 177 continues to read $S_H$ and increase use-measure "t" every X minutes and cycle through the blocks as described above while the equipment is "on". When the equipment is turned "off", the values of $P_H$, $S_{Hi}$, and "t" remain in memory such that when the equipment is again turned "on", method 177 starts in block 143 and continues the cycle of stepping through the blocks to determine and, when necessary, give warnings about fuel concentration in fluid.

In this manner, method 177 essentially continuously monitors the fuel dilution of a fluid and sends warnings based on the concentration of fuel in the fluid and the fluid's ability to handle the fuel contained therein.

The embodiment of FIG. 15 reads and uses lubricant response $S_H$ essentially immediately after the equipment is turned "on". As was described with reference to FIG. 14, response reading may start some time after start-up to allow the lubricant to reach steady-state operating conditions. This is used where the lubricant must be read at essentially a constant temperature as in the embodiments of FIGS. 14, 15. The method of the invention, however, is not limited to reading lubricant responses at an essentially constant temperature.

Figure 16:
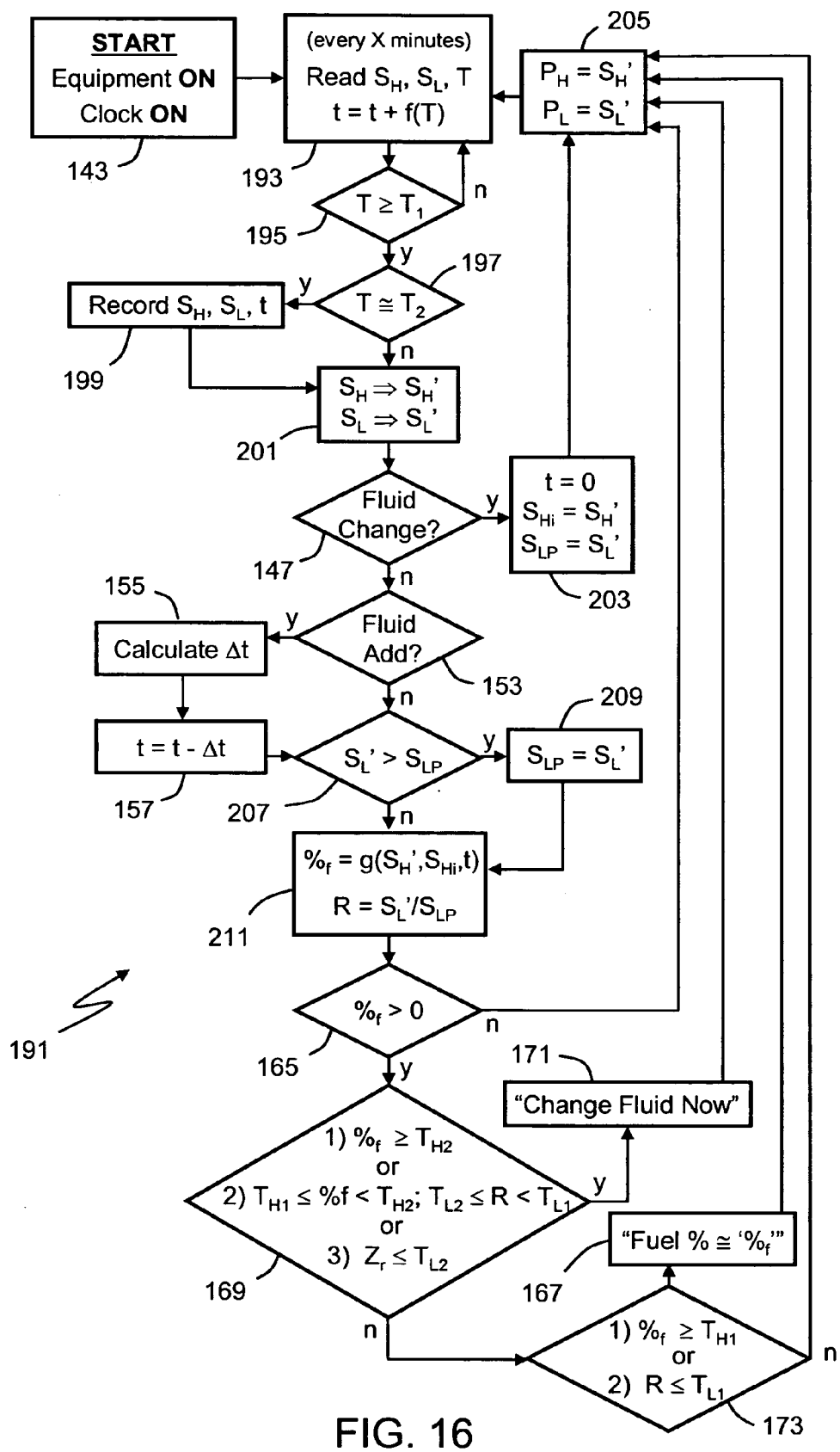
FIG. 16 is a flow chart of a feature of the present invention wherein high-frequency permittivity response data and low-frequency real impedance data are compensated for temperature variations and used to determine and output lubricant condition.

FIG. 16 shows an embodiment of a feature of the present invention for use in determining the fuel dilution condition of a lubricant in equipment where the lubricant responses $S_H$, $S_L$ are corrected or compensated for lubricant temperature variations such that the resulting response values $S_H'$, $S_L'$ are essentially equal to the responses that would have been read if the lubricant were at a desired fixed temperature T*. To aid in describing the embodiment, those blocks that are the same as in a previous embodiment are labeled the same.

Referring to FIG. 16, method 191 begins in block 143 when the equipment is turned "on", and a clock is turned "on". As in the previous embodiments, time is the measure of equipment use to determine permittivity change slope. After start-up, method 191, in addition to reading responses $S_H$ and $S_L$, reads temperature of the lubricant T, and increases the time since the last complete lubricant change "t" by an amount f(T). The function f(T) is equal to X when the equipment is at a desired operating temperature T*. However, when the equipment is not at that T*, the effective use-measure, that is, a use-measure that more accurately predicts the no-fuel high-frequency $\epsilon/\epsilon_i$, is a time value that varies as a function of temperature. Progressing to block 195, method 191 determines if the lubricant temperature T is greater than a first temperature threshold $T_1$, which is the lower temperature limit for the temperature correcting or compensating functions that are described below. If the determination of block 195 is "no" then method 191 returns to block 193 to read $S_H$, $S_L$, T and increase use-measure "t" by the appropriate amount. The method cycles between 193 and 195 until the determination in block 195 is "yes" and the method advances to block 197 to determine if the lubricant temperature T approximately equals to a fixed temperature $T_2$. If the determination is "yes", in block 199 the responses $S_H$, $S_L$ and lubricant use-measure "t" are recorded. In method embodiment 191, fluid condition is determined using temperature compensated high and low frequency responses to allow for essentially continuous lubricant condition determination in equipment where lubricant temperature varies. The lubricant condition determination with temperature compensated response, however, can have greater error than a determination using fixed temperature responses. Hence, the actual lubricant responses at the operating temperature $T_2$, which can equal the desired operating T*, recorded in block 199 may be used either as part of the on-line lubricant condition determination or for off-line analysis as a check of the determination made using temperature corrected lubricant responses. If the determination of block 197 is "no" or after recording data in block 199, method 191 in block 201 temperature compensates the responses $S_H$, $S_L$ such that the resulting $S_H'$, $S_L'$ are essentially the high and low frequency responses respectively if the responses had been measured at a desired fixed temperature T*. That is, at temperature T* $S_H'=S_H$ and $S_L'=S_L$. The temperature compensation of block 201 can be written as $S_H'=a(S_H,T)$ and $S_L'=b(S_L,T)$ where the functions $a(S_H,T)$ and $b(S_L,T)$ can each be a formula, a look-up table or combinations thereof that temperature compensates the high-frequency response and low-frequency response respectively. Temperature compensation is effective over a limited temperature range because of the complex manner in which lubricant responses are affected by temperature when the frequencies of the applied signals are held fixed. Hence, temperature $T_1$ of block 195 is chosen as the lower limit of the temperature compensation range, that is, the lowest temperature where the temperature is acceptably accurate. In general, the applied high and low frequencies and electrode geometries are chosen so that the upper limit of the temperature compensation is beyond the maximum operating temperature T than can be expected for the lubricant. In this manner, the resulting $S_H'$, $S_L'$ of block 201 are a good representation of the lubricant responses to the applied signal if the temperature were at an essentially constant temperature T* as is the case for the embodiments of FIGS. 14 and 15. Hence, $S_H'$, $S_L'$ are used in the subsequent blocks of method 191 to determine the fuel dilution condition of the monitored lubricant as will now be explained.

After the temperature compensation of block 201, in block 147 method 191 determines if the lubricant was changed since the previous responses $P_H$, $P_L$. That determination can be based on an additional input to method 191, or can be based on a comparison of the current and previous responses $S_H'$, $S_L'$ and $P_H$, $P_L$ respectively as previously described. If the determination of block 147 is "yes", in block 203 use-measure "t" is set equal to zero, the initial high-frequency response $S_H$ is set equal to $S_H'$, and the peak low-frequency response $S_L$ is set equal to $S_L'$, after which in block 205 the previous high-frequency response $P_H$ is set equal to $S_H'$ and the previous low-frequency response $P_L$ is set equal to $S_L'$ before method 191 returns to block 193 to begin the cycle again. If the determination of block 147 is "no", method 191 determines in block 153 if fresh lubricant was added since the previous cycle of the method. If the determination is "yes", then as previously described an offset use-measure Δt is calculated tin block 155 and subtracted from use-measurement "t" in block 157. After offsetting "t" in block 157 or with a "no" determination in block 153, in block 207 method 191 determines if the temperature compensated low-frequency response $S_L'$ is greater than the stored low-frequency peak response $S_{LP}$. If the determination is "yes" then in block 209 $S_{LP}$ is replaced with $S_L'$. If the determination of block 207 is "no" or after block 209, in block 211 a percent fuel concentration %$_f$ or an equivalent is calculated, knowing the current the temperature compensated $S_H'$, the initial $S_{Hi}$, and the lubricant use-measure "t", as represented by the function $g(S_H',S_{Hi},t)$. The calculation can be done using formulae, look-up tables or combinations thereof, such that the ratio $\epsilon/\epsilon_i$ or equivalent is compared to a predicted $\epsilon/\epsilon_i$ or equivalent based on use-measure "t" to estimate the fuel concentration in the lubricant. Also in block 211, the variable R is set equal to the temperature compensated low-frequency lubricant response $S_L'$ divided by the peak low-frequency response $S_{LP}$.

In block 165, the method 191 determines if fuel dilution %$_f$ calculated in block 211 is greater than zero. If the determination is "no", then method 191 in block 205 resets the previous values $P_H$, $P_L$ and returns to block 193 to, X minutes after the previous reading, read $S_H$, $S_L$, T and increase lubricant use-measure "t" by a temperature compensated amount f(T). If the determination of block 165 is "yes", then in block 169 the method 191 determines if the estimated fuel concentration %$_f$ is greater than or equal to a threshold $T_{H2}$, or if the real impedance ratio R is less than or equal to threshold $T_{L2}$, or if the estimated fuel concentration %$_f$ is less than threshold $T_{H2}$ but greater than or equal to a threshold $T_{H1}$ and the real impedance ratio R is greater than threshold $T_{L2}$ but less, than or equal to a threshold $T_{L1}$. That is, block 169 determines if the fuel dilution %$_f$ is greater than a fuel condemnation threshold $T_{H2}$, if the real impedance ratio is less than the low frequency condemnation threshold $T_{L2}$, or if both the fuel dilution and the impedance ratio are between initial warning thresholds $T_{H1}$, $T_{L1}$ respectively and the condemnation thresholds $T_{H2}$, $T_{L2}$ respectively. If the determination of block 169 is "yes", then method 191 in block 171 sends a signal that the lubricant has reached the end of its useful life and needs to be changed now. After sending the warning signal, method 191 resets the previous signals $P_H$, $P_L$ in block 205 and returns to block 193 to read $S_H$, $S_L$, T and to increase "t" at the appropriate time. If the determination of block 169 is "no", a determination is made in block 173 if either %$_f$ is greater than or equal to initial warning threshold $T_{H1}$, or the real impedance ratio R is less than or equal to initial warning threshold $T_{L1}$. If the determination is "yes", then method 191 in block 167 sends a signal that the lubricant contains the estimated fuel concentration %$_f$. If the determination block 173 is "no" then no warning message is send. In either case, after sending the signal in block 175 or after a "no" determination in block 173, method 191 resets the previous signals $P_H$, $P_L$ in block 205 and returns to block 193 to read $S_H$, $S_L$, T and increase "t" at the appropriate temperature corrected time and begin the cycle again.

Method 191 continues to read $S_H$, $S_L$, T and increase use-measure "t" every X minutes and cycle through the blocks as described above while the equipment is "on". When the equipment is turned "off", the values of $P_H$, $P_L$, $S_{Hi}$, $S_{LP}$ and "t" remain in memory such that when the equipment is again turned "on", method 191 starts in block 143 and continues the cycle of stepping through the blocks to determine and, when necessary, give outputs about lubricant's fuel condition.

In this manner, method 191 essentially continuously monitors the fuel dilution of a lubricant when lubricant temperature is greater than or equal to temperature $T_1$ and sends outputs based on the concentration of fuel in the lubricant and on the lubricant's ability to handle the fuel contained therein.

While method 141, 177, 191 of FIGS. 14, 15, 16 respectively use fixed thresholds $T_{H1}$, $T_{H2}$, $T_{L1}$, $T_{L2}$ for all lubricant formulations and all equipment/engine applications. Other invention embodiments can allow the thresholds to be updated based on information inputted to the method. Further other invention embodiments can allow the equations, look-up tables, or combinations thereof used to temperature compensate the lubricant responses to be up dated. Further other invention embodiments can allow the equation, look-up tables or combinations thereof used to determine the percent fuel %$_f$ to be updated for changes in, for example, lubricant formulation, equipment use or duty cycle, fuel type, or others.

Figure 17:
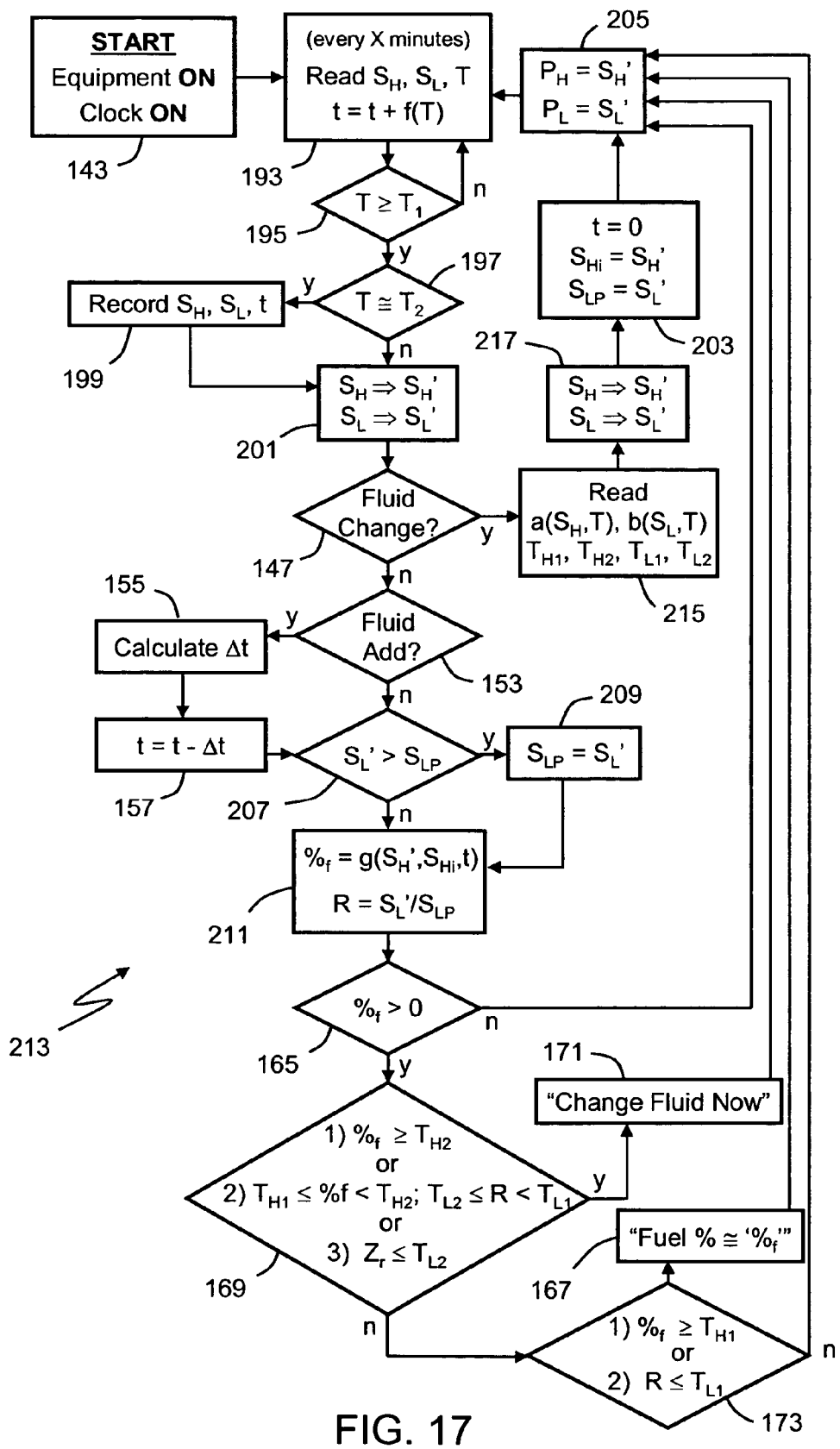
FIG. 17 is a flow chart of a feature of the present invention wherein threshold values and temperature compensation functions can be updated by external input.

FIG. 17 shows an embodiment of a feature of the present invention for use in determining the fuel dilution condition of a lubricant where the lubricant responses $S_H$, $S_L$, are corrected for variations of lubricant temperature and where information need to determine the fuel-dilution condition of a lubricant can be updated each time a complete lubricant is made. The embodiment of FIG. 17 is the same as the embodiment of FIG. 16 except for the addition of two blocks. Hence, all blocks of FIG. 17, except for the two additional blocks, are labeled the same as the equivalent blocks of FIG. 16, and the following describes differences due to the two added blocks.

Referring to FIG. 17, method 213 begins in block 143 when the equipment is turned "on" thereby turning the lubricant use-measure, the clock, "on". The lubricant responses $S_H$, $S_L$ and temperature T are read and the use-measure "t" increased a temperature-corrected time at X minute intervals in block 193. If the temperature T is below temperature $T_1$, the method 213 cycles between blocks 193 and 195, progressing to block 197 only if T is greater than or equal to $T_1$. If T is determined to be approximately equal to temperature $T_2$ in block 197 then $S_H$, $S_L$ and "t" are recorded in block 199. If T is not approximately equal to $T_2$ or after recording the values in block 199, the high and low frequency lubricant responses $S_H$, $S_L$ are converted to temperature compensated responses $S_H'$, $S_L'$ in block 201 as described in conjunction with the method 191 of FIG. 16 where the temperature compensation of block 201 can be written: $S_H'=a(S_H,T)$ and $S_L'=b(S_L,T)$, and the functions $a(S_H,T)$ and $b(S_L,T)$ can each be a formula, a look-up table or combinations thereof. In block 147 method 213 determines if a complete fluid change occurred since the last time that the method cycled through block 147. If the determination of block 147 is "yes", then method 213 in block 215 reads one or more inputs to determine if temperature compensation functions $a(S_H,T)$ or $b(S_L,T)$ are being updated or if thresholds $T_{H1}$, $T_{H2}$, $T_{L1}$, or $T_{L2}$ are being updated to allow a more appropriate determination of the fresh lubricant's fuel condition as the lubricant is used. The data read in block 215 can be information inputted by, for example, a keypad, optical scanner, or other means and stored in memory when the lubricant change occurred, or can be already stored information where an external input or a marker in the fresh lubricant is monitored to select which data to read for the particular fresh lubricant. If method 213 reads updated values for the functions or thresholds in block 215, the new values are used by the method until the next time the values are updated in block 215. In block 217 temperature compensated values for $S_H'$, $S_L'$ are calculated so that should updated compensation function $a(S_H,T)$ or $b(S_L,T)$ be read in block 215, the initial high-frequency response $S_{Hi}$ and the starting point for the peak low-frequency response $S_{LP}$ are properly set in block 203.

The remaining blocks of the method 213 are the same as the blocks of method 191 of FIG. 191, and the lubricant fuel-dilution condition determination and outputs are the same. The only difference is that method 213 is making the determinations in block 207, 211, 169 and 173 using functions and thresholds that can be updated in block 215 of the method, whereas the method 191 has fixed functions and thresholds. After the functions and thresholds are updated in block 215, however, method 213 holds those functions and thresholds fixed until the next time new temperature compensation functions or thresholds are updated in block 215.

In this manner, information can be input to method 213 that allows the method to be optimized for the essentially continuously monitoring of output of the fuel dilution condition of a lubricant when the lubricant temperature is greater than or equal to temperature $T_1$.

While method 213 of FIG. 17 can read inputs of new temperature compensation functions and thresholds when a complete lubricant change occurs, other embodiments of the invention read other information that is meaningful for the determination of the fuel dilution condition of a lubricant, for example the function $g(S_H',S_H i,t)$ can be updated if necessary, or values for the initial high-frequency response $S_{Hi}$ or of the peak low-frequency response $S_{LP}$ can be read as inputs instead of set or determined as in method 213. Also inputted information can be read at times other than after a complete lubricant change, for example information can be read each time the equipment is turned "on" and/or each time fluid responses $S_H$ and $S_L$ are read.

While method 191 of FIG. 16 uses fixed functions to compensate lubricant responses for temperature variation and method 213 of FIG. 17 allows updating the temperature compensation functions with external input, other invention embodiments of the invention can allow the temperature compensation to be updated as part of the method.

While particular embodiments of the present invention have been shown and described, it is apparent that various combinations, changes and modification may be made therein to monitor and report the fuel dilution condition of a lubricant in various applications without departing from the invention in its broadest aspects. In particular, with regard to various functions performed by the above described invention, the terms (including any reference to a "means") used to describe individual components or sub-systems of the invention are intended to correspond, unless otherwise indicated, to any component or sub-system which performs the specified function of the described component or sub-system (e.g. that is functionally equivalent), even though not structurally or electronically equivalent to the described component or sub-system which performs the function in the herein illustrated embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A method for determining the fuel-dilution condition of a lubricant comprising:
   a. applying a high-frequency voltage signal between electrodes immersed in a fluid,
   b. measuring the lubricant dependent response to the applied high-frequency signal and determining a ratio of a high-frequency lubricant property to the high-frequency property when the lubricant is fresh, and
   c. comparing at least one of the following properties selected from the group consisting of the determined high-frequency lubricant property ratio to a ratio predicted based on use since the lubricant was fresh, a change in the determined high-frequency lubricant property ratio as a function of use to a change predicted use-based change, and combination thereof, to estimate the fuel content of the lubricant,
wherein the applied signal is selected from at least one of the group consisting of essentially sinusoidal with an essentially defined frequency, essentially non-sinusoidal of frequency defined by the Fourier-transform base frequency, and combination thereof wherein each step is conducted continuously, intermittently, repeatedly and combinations thereof.

2. The method of claim 1 wherein the method further comprises:
   a. applying an essentially sinusoidal low-frequency voltage signal between electrodes immersed in the fluid,
   b. measuring a lubricant dependent response to the applied low-frequency signal and determining a ratio of a low-frequency property to a peak low-frequency property measured since the lubricant was fresh, and
   c. comparing the determined low-frequency property ratio to at least one property ratio threshold, to determine the lubricant's ability to control the fuel content,
wherein the a threshold for comparing the determined low-frequency property ratio is selected from at least one form the group consisting of fixed, updated by external input and combinations thereof wherein each step is conducted continuously, intermittently, repeatedly and combinations thereof.

3. The method of claim 2 wherein the lubricant response to the applied signal is measured at essentially fixed temperature with the temperature dependent upon the fluid employed, and wherein the temperature variation is less than 5° C. and wherein the applied frequency is in the range of about 1 Hz to about 1 kHz.

4. The method of claim 2 wherein the lubricant response to the applied signal is measured at variable temperatures in the range of ambient temperatures to maximum operating temperatures and wherein the lubricant property determination is selected from at least one of the group consisting of converting the property to essentially a fixed-temperature property, minimizing the effect of temperature variation using a temperature dependent formula, using a temperature dependent look-up table and combinations thereof.

5. The method of claim 4 wherein the means for converting the fluid property to essentially fixed-temperature fluid property is selected from at least one of the group consisting of fixed, updated by external input, automatically updated when fluid temperature increases between two temperature thresholds at greater than a preset rate and combinations thereof.

6. The method of claim 2 wherein the determined low-frequency lubricant property is selected from at least one of the group consisting of real impedance, real impedance equivalent and combinations thereof.

7. The method of claim 2 that further includes resetting and updating values used for the comparisons under the conditions selected from the group consisting of an external input is provided that a fluid change has occurred, change in the determined fluid property is used to that a fluid change has occurred and combinations thereof.

8. An apparatus that collects data required for on-line monitoring and detecting fuel-dilution condition of a lubricant by the method of claim 2.

9. The method of claim 1 wherein the frequency of the applied signal is predetermined as a function of at least one of the following selected from the group consisting of electrode geometry, lubricant temperature, lubricant temperature range, composition of the lubricant being monitored and combinations thereof.

10. The method of claim 1 wherein the lubricant response to the applied signal is measured at essentially fixed temperature with the temperature dependent upon the fluid employed, and wherein the temperature variation is less than about 5° C. and wherein the applied frequency is in the range of about 10 kHz to about 10 MHz.

11. The method of claim 1 wherein the lubricant response to the applied signal is measured at variable temperatures in the range of ambient temperatures to maximum operating temperatures and the lubricant property determination is selected from at least one of the group consisting of converting the property to essentially a fixed-temperature property, minimizing the effect of temperature variation, using a temperature dependent formula, using a temperature dependent look-up table and combinations thereof.

12. The method of claim 11 wherein the method for converting the fluid property to essentially fixed-temperature fluid property is selected from at least one of the group consisting of fixed, updated by external input, automatically updated when fluid temperature increases between two temperature thresholds at greater than a preset rate and combinations thereof.

13. The method of claim 1 wherein the determined high-frequency lubricant property is selected from at least one of the group consisting of permittivity, permittivity-equivalent and combinations thereof.

14. The method of claim 1 wherein the comparison used to estimate fuel content of the lubricant is made using a formula, a look-up table or combinations thereof.

15. The method of claim 1 wherein the comparison used to estimate fuel content of the lubricant is selected from at least one of the group consisting of fixed, updated by external input, updated by a determination that a complete lubricant change has occurred, updated by a determination that an addition of fresh lubricant was made, and combinations thereof.

16. The method of claim 1 wherein the lubricant use is measured based on at least one of the group consisting of equipment use-measure, a lubricant condition determined by other than the applied signals of this invention, and combinations thereof and wherein the use is measured from the point when the lubricant is fresh.

17. The method of claim 16 wherein equipment use-measure is selected from at least one of the group consisting of operating time, energy output, distance traveled, number of operating cycles, equipment temperature, fuel consumed, start/stop cycle and combinations thereof.

18. The method of claim 16 wherein lubricant condition is determined by at least one of the group consisting of lubricant response to one or more signals applied at frequencies other than the high-frequency signal of claim 1, viscosity, IR absorption, lubricant temperature and combinations thereof.

19. The method of claim 1 wherein the change of the determined high-frequency property is at least one selected from the group consisting of rate of property change as a function of lubricant use, the curvature of the property change as a function of lubricant use, and combinations thereof.

20. The method of claim 1 further includes resetting and updating values used for the comparisons under the conditions selected from the group consisting of an external input is provided that a fluid change has occurred, change in the determined fluid property is used to determine that a fluid change has occurred and combinations thereof.

21. An apparatus that collects data required for on-line monitoring and detecting fuel-dilution condition of a lubricant by the method of claim 1.

22. An apparatus that monitors and detects the fuel-dilution condition of a lubricant comprising:
   d. applying a high-frequency voltage signal between electrodes immersed in a fluid,
   e. measuring a lubricant response to the applied high-frequency signal and determining a ratio of a high-frequency lubricant property to the high-frequency property when the lubricant is fresh, and
   f. comparing at least one of the following selected from the group consisting of the determined high-frequency lubricant property ratio to a ratio predicted based on use since the lubricant was fresh, a change in the determined high-frequency lubricant property ratio as a function of use to a change predicted use-based change, and combination thereof to estimate a fuel content of the lubricant, wherein the applied signal is selected from at least one of the group consisting of essentially sinusoidal with an essentially defined frequency, essentially non-sinusoidal of frequency defined by the Fourier-transform base frequency, and combination thereof wherein each step is conducted continuously, intermittently, repeatedly and combinations thereof.

23. The apparatus of claim 22 where the apparatus further comprises:
   a. applying an essentially sinusoidal low-frequency voltage signal between electrodes immersed in the fluid,
   b. measuring a lubricant dependent response to the applied low-frequency signal and determining a ratio of a low-frequency property to a peak low-frequency property measured since the lubricant was fresh, and
   c. comparing the determined low-frequency property ratio to at least one property ratio threshold, to determine the lubricant's ability to control the fuel content, wherein the a threshold for comparing the determined low-frequency property ratio is selected from at least one form the group consisting of fixed, updated by external input and combinations thereof wherein each step is conducted continuously, intermittently, repeatedly and combinations thereof.

* * * * *